(12) United States Patent
Zhang et al.

(10) Patent No.: US 11,642,047 B2
(45) Date of Patent: *May 9, 2023

(54) INTERACTIVE TRAINING OF BODY-EYE COORDINATION AND REACTION TIMES USING MULTIPLE MOBILE DEVICE CAMERAS

(71) Applicant: NEX Team Inc., San Jose, CA (US)

(72) Inventors: Qi Zhang, Hong Kong (HK); Arron Mollet, San Jose, CA (US); Wing Hung Chan, Hong Kong (HK); Keng Fai Lee, Cupertino, CA (US)

(73) Assignee: NEX Team Inc., San Jose, CA (US)

( * ) Notice: Subject to any disclaimer, the term of this patent is extended or adjusted under 35 U.S.C. 154(b) by 27 days.

This patent is subject to a terminal disclaimer.

(21) Appl. No.: 17/179,435

(22) Filed: Feb. 19, 2021

(65) Prior Publication Data
US 2021/0174700 A1    Jun. 10, 2021

Related U.S. Application Data

(63) Continuation of application No. 16/792,190, filed on Feb. 15, 2020, now Pat. No. 10,930,172, which is a
(Continued)

(51) Int. Cl.
*G06K 9/00* (2022.01)
*G09B 19/00* (2006.01)
(Continued)

(52) U.S. Cl.
CPC ...... *G09B 19/0038* (2013.01); *A63B 24/0062* (2013.01); *A63B 24/0075* (2013.01);
(Continued)

(58) Field of Classification Search
CPC ........ G06K 9/00; G06K 9/00724; G06K 9/46; G06K 9/00342; G06N 3/08; G06T 7/11;
(Continued)

(56) References Cited

U.S. PATENT DOCUMENTS 6,307,576 B1   10/2001   Rosenfeld
9,886,624 B1   2/2018   Marty et al.
(Continued)

OTHER PUBLICATIONS

Krzysztof Przednowek, et al., "A System for Analysing the Basketball Free Throw Trajectory Based on Particle Swarm Optimization," Applied Sciences, 2018, vol. 8, Issue 11, p. 2090, IWDPI, Basel, Switzerland.
(Continued)

*Primary Examiner* — Omkar A Deodhar
(74) *Attorney, Agent, or Firm* — American Patent Agency PC; Daniar Hussain; Stephen M. Hou

(57) ABSTRACT

Methods and systems for multi-player training of body-eye coordination using mobile computing devices each having a camera are provided. The methods and systems execute instructions to capture a first training video of a first of player, using a first camera on a first mobile computing device; superimpose a visual cue onto the first training video at a visual cue location and for a cue period starting from a first time instant; determine whether the first player has responded to the visual cue at a second time instant within the cue period; receive a notification from a second mobile computing device, where the notification was generated in response to determining that a second player has responded to the visual cue at a third time instant within the cue period; and in response to a determination that the first player has responded to the visual cue and to the notification, generate a feedback to the first player.

20 Claims, 27 Drawing Sheets

Related U.S. Application Data continuation of application No. 16/555,812, filed on Aug. 29, 2019, now Pat. No. 10,600,334.

(60) Provisional application No. 62/778,244, filed on Dec. 11, 2018.

(51) Int. Cl.

| | |
|---|---|
| *G06K 9/62* | (2022.01) |
| *G06N 3/08* | (2023.01) |
| *A63B 71/06* | (2006.01) |
| *A63B 24/00* | (2006.01) |
| *G06V 20/40* | (2022.01) |
| *A61B 5/11* | (2006.01) |
| *A63B 69/00* | (2006.01) |

(52) U.S. Cl.
CPC ...... *A63B 71/0622* (2013.01); *A63B 71/0669* (2013.01); *G06K 9/6256* (2013.01); *G06N 3/08* (2013.01); *G06V 20/46* (2022.01); *A61B 5/1128* (2013.01); *A63B 69/0071* (2013.01); *A63B 2071/063* (2013.01); *A63B 2071/0694* (2013.01); *A63B 2220/806* (2013.01)

(58) Field of Classification Search
CPC ........... G06T 2207/30221; G09B 19/00; A63F 2009/2435
See application file for complete search history.

(56) References Cited

U.S. PATENT DOCUMENTS

| | | | |
|---|---|---|---|
| 10,010,778 | B2 | 7/2018 | Marty et al. |
| 2005/0143154 | A1 | 6/2005 | Bush |
| 2013/0095961 | A1 | 4/2013 | Marty |
| 2017/0213087 | A1 | 7/2017 | Chen |
| 2018/0189971 | A1 | 7/2018 | Hildreth |
| 2018/0218243 | A1 | 8/2018 | Felsen et al. |
| 2018/0322337 | A1 | 11/2018 | Marty |
| 2019/0087661 | A1 | 3/2019 | Lee et al. |

OTHER PUBLICATIONS

Simone Francia, "SpaceJam: a Dataset for Basketball Action Recognition," Github Code Repository Page, available at: https://github.com/simonefrancia/SpaceJam, last access: Apr. 2, 2019.

Techsmith Corporation, "Coach's Eye," Coach's Eye website, available at: https://www.coachseye.com/, last accessed: Feb. 18, 2019.

Stats LLC, "Stats SportVU Basketball Player Tracking," SportVU website, available at: https://www.stats.com/sportvu-basketball/, last accessed: Feb. 12, 2019.

Vignesh Ramanathan, et al., "Detecting events and key actors in multi-person videos," The IEEE Conference on Computer Vision and Pattern Recognition (CVPR), 2016, pp. 3043-3053.

Mark Sandler, et al., "MobileNetV2: Inverted Residuals and Linear Bottlenecks," The IEEE Conference on Computer Vision and Pattern Recognition (CVPR), 2018, pp. 4510-4520, available at: https://arxiv.org/abs/1801.04381, last accessed: May 7, 2019.

Wei Liu, et al., "SSD: Single Shot MultiBox Detector," European conference on computer vision, pp. 21-37, Springer, Cham, 2016, available at: https://arxiv.org/abs/1512.02325, last accessed: May 7, 2019.

Zhe Cao, et al., "Realtime Multi-Person 2D Pose Estimation using Part Affinity Fields," Proceedings of the IEEE Conference on Computer Vision and Pattern Recognition, pp. 7291-7299, 2017, available at: https://arxiv.org/abs/1611.08050, last accessed: May 7, 2019.

Andrew G. Howard, et al., "MobileNets: Efficient Convolutional Neural Networks for Mobile Vision Applications," arXiv preprint arXiv:1704.04861, 2017, available at: https://arxiv.org/abs/1704.04861, last accessed: May 7, 2019.

Raine Kajastila, et al., "Motion Games in Real Sports Environments," XXII.2 Mar. + Apr. 2015, Available at: https://interactions.acm.org/archive/view/march-april-2015/motion-games-in-real-sports-environments, ast accessed May 21, 2019.

Raine Kajastila, et al., "Empowering the Exercise: a Body-Controlled Trampoline Training Game," International Journal of Computer Science in Sport-vol. 13/2014/Edition 1, Available at: www.iacss.org.

Raine Kajastila, et al., "Augmented Climbing: Interacting With Projected Graphics on a Climbing Wall," CHI 2014, Apr. 26-May 1, 2014, Toronto, ON, Canada, ACM 978-1-4503-2474-8/14/04. Available at: http://dx.doi.org/10.1145/2559206.2581139, last accessed May 22, 2019.

Perttu Hamalainen, Tommi Llmonen, et al., "Martial Arts in Artificial Reality," CHI 2005 PAPERS: Enhancing Virtual Spaces and Large Displays, Apr. 2-7, Portland Oregon, US.

Rainer Planinc, et al., "Exergame Design Guidelines for Enhancing Elderly's Physical and Social Activities," Ambient 2013 : The Third International Conference on Ambient Computing, Applications, Services and Technologies, Available at: https://pdfs.semanticscholar.org/80d7/ddb6d443ef693fd59e12b5413a2a142ef6da.pdf.

Kazumoto Tanaka et al., "A Comparison of Exergaming Interfaces for Use in Rehabilitation Programs and Research," The Journal of the Canadian Game Studies Association, vol. 6(9): 69-81, 2012, Available at: http://loading.gamestudies.ca.

Andy Butler, et al., "Nike 'House of Mamba' LED Basketball Court by AKQA", Aug. 16, 2014, Available at: https://www.designboom.com/design/nike-house-of-mamba-led-basketball-court-08-16-2014/, last accessed Jun. 18, 2019.

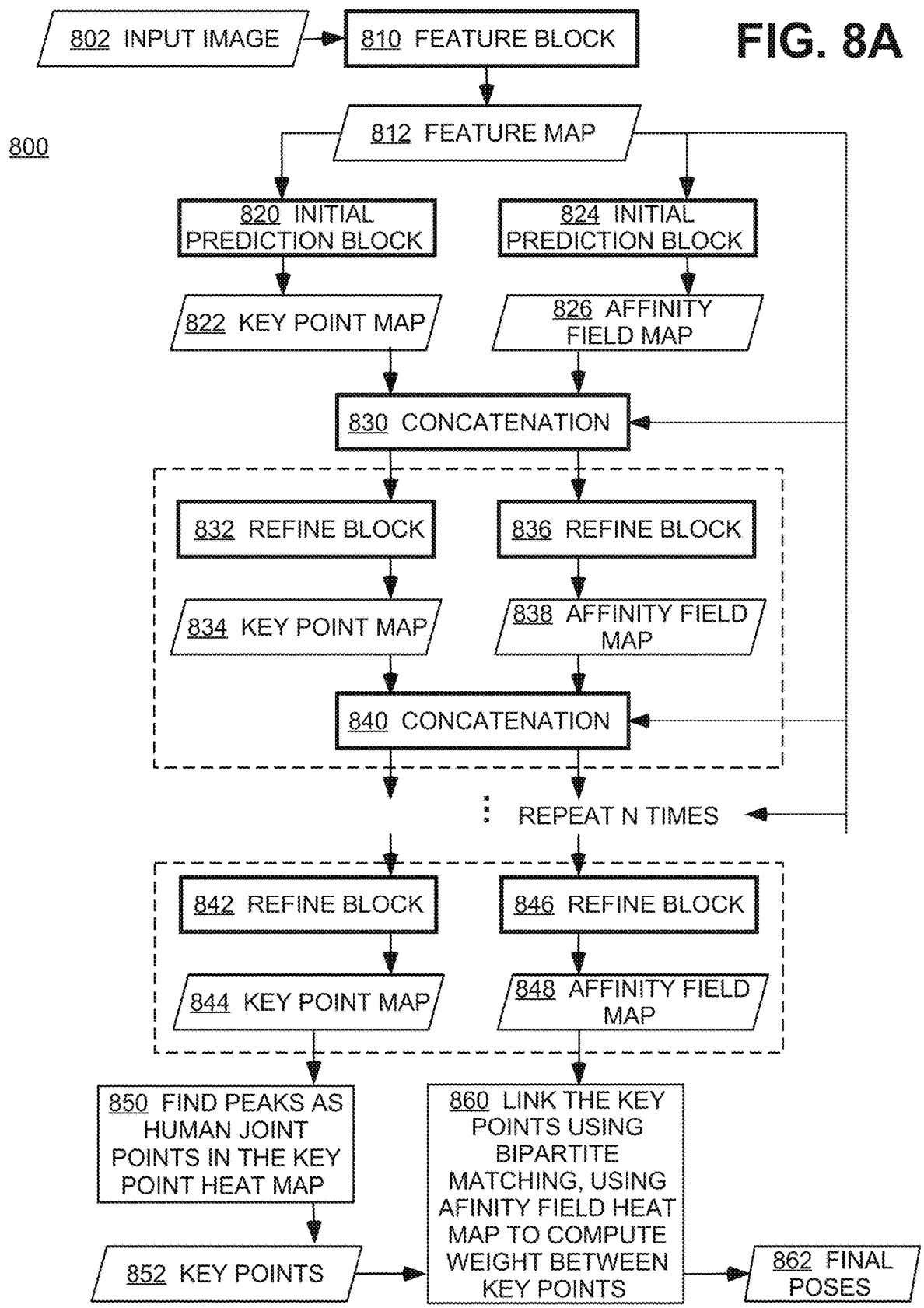

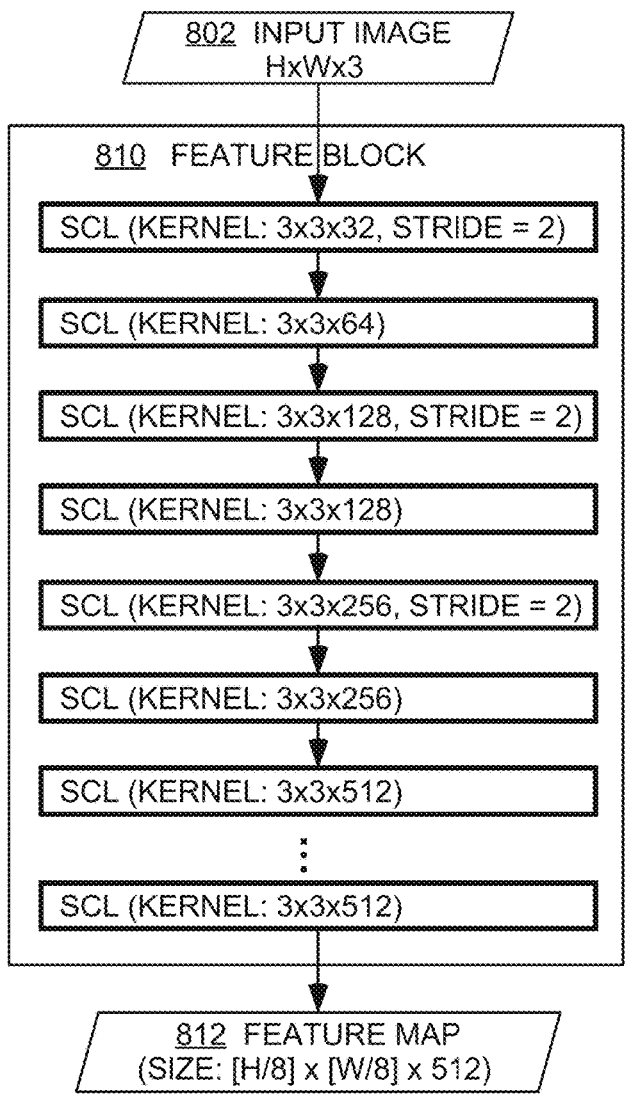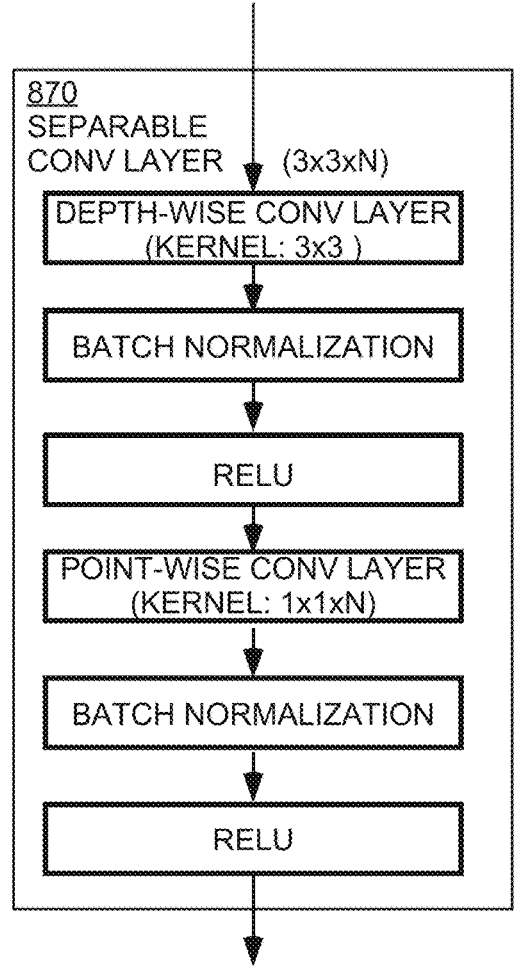
FIG. 8B
FIG. 8C

INTERACTIVE TRAINING OF BODY-EYE COORDINATION AND REACTION TIMES USING MULTIPLE MOBILE DEVICE CAMERAS

REFERENCE TO RELATED APPLICATIONS

This application is a continuation of U.S. Ser. No. 16/792,190, filed on Feb. 15, 2020, entitled "Methods and Systems For Facilitating Interactive Training of Body-Eye Coordination and Reaction Time", which itself is a continuation of U.S. Ser. No. 16/555,812, filed on Aug. 29, 2019, entitled "Methods and Systems For Facilitating Interactive Training of Body-Eye Coordination and Reaction Time", which itself is a non-provisional of and claims priority to provisional U.S. Ser. No. 62/778,244, filed on Dec. 11, 2018, entitled "Methods and Systems for Facilitating Training of Hand-Eye Coordination and Reaction Time".

This application is also related to non-provisional U.S. Ser. No. 16/109,923, filed on Aug. 23, 2018, entitled "Methods and Systems for Ball Game Analytics with a Mobile Device", and is also related to U.S. Ser. No. 16/445,893, filed on Jun. 19, 2019, entitled "Remote Multiplayer Interactive Physical Gaming with Mobile Computing Devices".

The entire disclosures of all referenced applications are hereby incorporated by reference in their entireties herein.

NOTICE OF COPYRIGHTS AND TRADEDRESS

A portion of the disclosure of this patent document contains material which is subject to copyright protection. This patent document may show and/or describe matter which is or may become tradedress of the owner. The copyright and tradedress owner has no objection to the facsimile reproduction by anyone of the patent disclosure as it appears in the U.S. Patent and Trademark Office files or records, but otherwise reserves all copyright and tradedress rights whatsoever.

FIELD OF THE INVENTION

Embodiments of the present invention are in the field of sports training, and pertain particularly to methods and systems for providing interactive virtual coaching for performance training with a mobile device, the mobile device having one or more cameras for video capture.

BACKGROUND OF THE INVENTION

The statements in this section may serve as a background to help understand the invention and its application and uses, but may not constitute prior art.

In both professional and amateur sports, good coaching is essential for the development of technical, tactical, physical and drill skills, and personalized and targeted training often help improve fitness and performance in a particular sport while reducing chances of injury. Advances in modern computing and networking technology have allowed virtual access to experienced coaches and effective performance training programs, yet existing digital coaching and training applications are either passive in nature, where users or players are provided with instructions or drilling plans only, or function in an offline manner, where video recordings of players in action can be replayed, analyzed, and annotated, manually by a coach or the player, after a training or drill session is completed.

More recently, real-time analytics systems have been developed to provide quantitative and qualitative game and player analytics, with uses in broadcasting, game strategizing, and team management, yet mass mainstream usage of such systems by individual players for customized performance training is still complex and expensive. Real-time tracking technology based on image recognition often requires use of multiple high-definition cameras mounted on top of a game area or play field for capturing visual data from multiple camera arrays positioned at multiple perspectives, calibration for different environments, and massive processing power in high-end desktop and/or server-grade hardware to analyze data from the camera arrays. Accurate tracking of player motion and forms, and real-time automated analysis require vast computational resources that hinder implementations with low-cost, general-purpose hardware with small form factors.

Therefore, it would be an advancement in the state of the art to allow interactive, real-time virtual coaching and performance training, including facilitating training of body-eye coordination and reaction time, using just a mobile device by utilizing video data captured from a camera on the mobile device.

It is against this background that various embodiments of the present invention were developed.

BRIEF SUMMARY OF THE INVENTION

Some embodiments of the present invention include methods, systems, and apparatuses for providing virtual coaching of a physical activity using a mobile device.

In particular, one embodiment is a non-transitory storage medium, the non-transitory storage medium storing executable instructions, the executable instructions when executed by a hardware processor causes the hardware processor to execute a process for facilitating multi-player training of body-eye coordination using mobile computing devices each having a camera. The non-transitory storage medium comprising executable instructions to capture a first training video of a first of player, using a first camera on a first mobile computing device; superimpose a visual cue onto the first training video at a visual cue location and for a cue period starting from a first time instant; determine whether the first player has responded to the visual cue at a second time instant within the cue period, by analyzing a body posture flow of the first player between the first time instant and the second time instant, wherein the body posture flow of the first player is extracted from the first training video by performing a computer vision algorithm on one or more frames of the first training video; receive a notification from a second mobile computing device, wherein the notification was generated in response to determining that a second player has responded to the visual cue at a third time instant within the cue period; and in response to a determination that the first player has responded to the visual cue and to the notification, generate a feedback to the first player.

In some embodiments, the determination that the second player has responded to the visual cue at the third time instant within the cue period comprises executable instructions to analyze a body posture flow of the second player between the first time instant and the third time instant, wherein the body posture flow of the second player was extracted from a second training video of the second player by performing the computer vision algorithm on one or more frames of the second training video, wherein the second training video was captured using a second camera on the second mobile computing device, and wherein the visual cue was superimposed onto the second training video at the visual cue location starting from the first time instant.

In some embodiments, the non-transitory storage medium further comprises executable instructions to generate the feedback based on an identity of at least one player that responded.

In some embodiments, the visual cue is a symbol superimposed onto the first training video at the first location of an image plane of the first training video.

In some embodiments, the determination whether one of the players has responded to the visual cue comprises determining a player movement to virtually touch the symbol in the image plane with a body part.

In some embodiments, the determination whether one of the players has responded to the visual cue comprises determining whether the at least one player has virtually touched the symbol in the image plane with a sports equipment object.

In some embodiments, the determination whether one of the players has responded to the visual cue comprises determining whether at least one player has performed a predetermined sequence of movements.

In some embodiments, the non-transitory storage medium further comprises executable instructions to determine a reaction time as a duration between the first time instant and the second time instant, wherein the feedback is a quality score generated based on the reaction time.

In some embodiments, the training comprises a plurality of difficulty levels based at least in part on a duration of the cue period.

In some embodiments, the computer vision algorithm comprises a Convolutional Neural Network (CNN) for detecting one or more key points of the first player in an image plane, and the CNN module has been trained using one or more prior videos.

In some embodiments, the training video comprises a dribbling activity, and the superimposing the first training video with the visual cue is in response to determining that at least one player has dribbled for a predetermined number of times before the first time instant.

In some embodiments, the non-transitory storage medium further comprises executable instructions to wait for a period of wait time before the superimposing the training video with the visual cue, wherein a duration of the wait time is based on a detected player action during the wait time.

In some embodiments, the first training video comprises a juggling activity, and the superimposing the training video with the visual cue is in response to determining that at least one player has juggled for a predetermined number of times before the first time instant.

In some embodiments, the non-transitory storage medium further comprises executable instructions to generate a training statistic for at least one player based on the training video, wherein the training video comprises a dribbling activity performed by the at least one player, and wherein the training statistic includes at least one of a reaction speed and a dribbling speed.

In some embodiments, the training statistic comprises a first current statistic that is associated with the training video and a second historical statistic that is associated with one or more historical training sessions associated with at least one player.

In some embodiments, the feedback is a score.

In some embodiments, the first training video comprise basketball training activities.

In some embodiments, the non-transitory storage medium further comprises executable instructions to receive a second notification from a third mobile computing device, wherein the second notification was generated based on a third training video of a third player, captured using a third camera on the third mobile computing device.

In another aspect, another embodiment is a system comprising a hardware processor and a non-transitory storage medium, the non-transitory storage medium storing executable instructions, the executable instructions when executed by the hardware processor causes the hardware processor to execute a process for facilitating multi-player training of body-eye coordination using mobile computing devices each having a camera, the executable instructions comprising instructions to execute the steps described herein.

In yet another aspect, one embodiment of the present invention is a mobile device having a camera, a hardware processor, and a non-transitory storage medium, the non-transitory storage medium storing executable instructions, the executable instructions when executed by the hardware processor cause the hardware processor to execute a process for facilitating training, the process comprising the steps described herein.

Yet other aspects of the present invention include methods, processes, and algorithms comprising the steps described herein, and also include the processes and modes of operation of the systems and servers described herein. Yet other aspects and embodiments of the present invention will become apparent from the detailed description of the invention when read in conjunction with the attached drawings.

BRIEF DESCRIPTION OF THE DRAWINGS

Embodiments of the present invention described herein are exemplary, and not restrictive. Embodiments will now be described, by way of examples, with reference to the accompanying drawings, in which:

FIG. 8A is a block diagram of an exemplary neural network for pose estimation, according to exemplary embodiments of the present invention;

FIG. 8B is a detailed block diagram illustrating an exemplary Feature Block, according to exemplary embodiments of the present invention;

FIG. 8C is a detailed block diagram illustrating an exemplary separable convolutional neural network layer, according to exemplary embodiments of the present invention;

DETAILED DESCRIPTION OF THE INVENTION

Figure 1A:
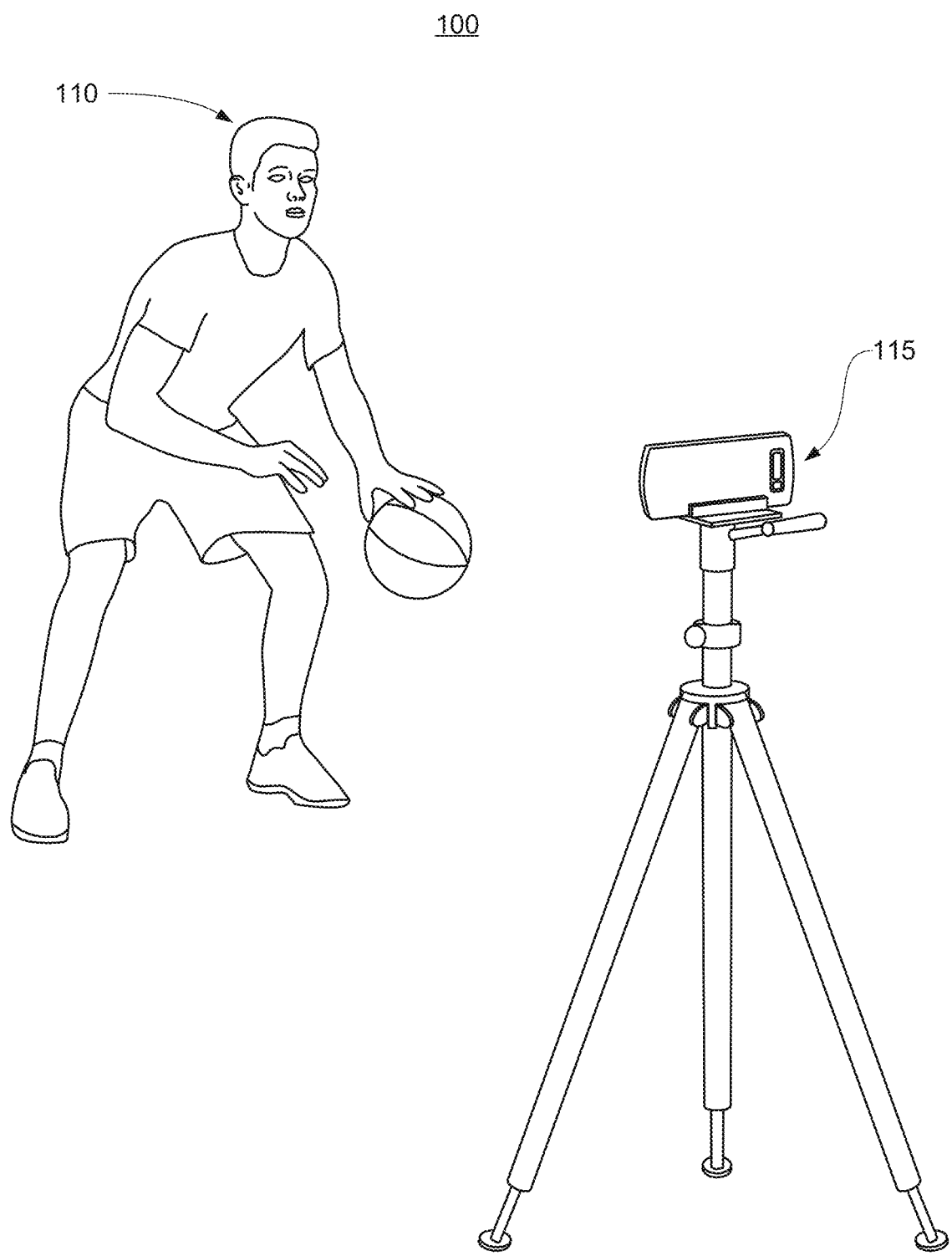
FIG. 1A is an exemplary setup for enabling interactive virtual coaching and training with a mobile computing device, according to some embodiments of the present invention.

In the following description, for purposes of explanation, numerous specific details are set forth in order to provide a thorough understanding of the invention. It will be apparent, however, to one skilled in the art that the invention can be practiced without these specific details. In other instances, structures, devices, activities, and methods are shown using schematics, use cases, and/or flow diagrams in order to avoid obscuring the invention. Although the following description contains many specifics for the purposes of illustration, anyone skilled in the art will appreciate that many variations and/or alterations to suggested details are within the scope of the present invention. Similarly, although many of the features of the present invention are described in terms of each other, or in conjunction with each other, one skilled in the art will appreciate that many of these features can be provided independently of other features. Accordingly, this description of the invention is set forth without any loss of generality to, and without imposing limitations upon the invention.

NEX, NEX TEAM, and HOMECOURT are trademark names carrying embodiments of the present invention, and hence, the aforementioned trademark names may be interchangeably used in the specification and drawing to refer to the products/services offered by embodiments of the present invention. The term NEX, NEX TEAM, or HOMECOURT may be used in this specification to describe the overall training video capturing, interactive coaching, and analytics generation platform, as well as the company providing said platform. With reference to the figures, embodiments of the present invention are now described in detail.

Introduction and Overview

Broadly, embodiments of the present invention relate to virtual coaching and pertain particularly to methods and systems for interactive, real-time virtual coaching and performance training for physical activities and sport games, using a mobile computing device having one or more on-device cameras, by deploying artificial-intelligence (AI)-based computer vision techniques.

It would be understood by persons of ordinary skill in the art that training or performance training activities discussed in this disclosure broadly refer to any physical exercise, workout, drill, or practice that improve a user's fitness and skill levels to better his or her ability to perform a given physical activity or sport. Training activities thus disclosed can maintain, condition, correct, restore, strengthen, or improve the physical ability, power, agility, flexibility, speed, quickness, reaction, endurance, and other physical and technical skills necessary for a physical activity or sport. Such a physical activity or sport may be competitive or non-competitive in nature, with or without specific goals or challenges, and may or may not be scored according to specific rules. A user of the system as disclosed herein is referred to as a player, including in non-competitive activities such as rehabilitative physical therapies and occupational therapies. A training session may involve one or more individual players. During a training session, individual skills such as power, speed, agility, flexibility, posture, balance, core strength, upper and lower-body strength, rhythm, swing, stroke, flick, running, stopping, dribbling, juggling, passing, catching, throwing, smashing, tackling, shooting, jumping, sprinting, serving, and goalkeeping may be isolated, broken down into specific movements, and worked upon. Such skills may be inter-dependent. For example, better core strength may lead to better stance and balance, and better body-eye and hand-eye coordination may lead to faster speed, shorter stopping time, and better control of a ball. Some training activities are tailored for specific demands of a particular sport. Embodiments of the present invention may be used for interactive virtual coaching in ball sports as well as other types of sports or physical activities, including but not limited to, basketball, soccer, baseball, football, hockey, tennis, badminton, juggling, archery, softball, volleyball, boxing, canoeing, kayaking, climbing, cycling, diving, equestrian, fencing, golf, gymnastics, handball, judo, karate, modern pentathlon, roller sport, rowing, rugby, sailing, shooting, swimming, surfing, table tennis, taekwondo, track and field, triathlon, water polo, weightlifting, wrestling, squash, wakeboard, wushu, dancing, bowling, netball, cricket, lacrosse, running, jogging, yo-yo, foot bagging, hand sacking, slinky, tops, stone skipping, and many other types of sports, games, and other activities in a similar fashion.

More specifically, in one aspect, embodiments of the virtual coaching system disclosed herein relate to providing audio or visual instructions, prompts, triggers, or cues for individual training activities or movements, tracking and analyzing player movements using one or more computer vision algorithms running on a mobile computing device such as a smartphone, tablet, or laptop, and optionally providing audio or visual feedback based on the movement analysis, in real-time or near real-time. Embodiments of the present invention may enable the mobile computing device to determine the level of body-eye coordination, hand-eye coordination, reaction time, and the like, from an analysis of training videos taken of the player during a training exercise.

A key feature of the present invention is the novel design of mobile AI-based computer vision techniques, to analyze player movements, generate player analytics and feedback, and facilitate interactive virtual coaching and training. Unlike existing computer vision-based monitoring systems that require dedicated sensor equipment such as high-resolution cameras mounted on top of a ball court or sensing bars mounted on top of a TV, embodiments of the present invention allow users to perform real-time monitoring, analysis and interactive training with a mobile device by utilizing simple on-device cameras and general-purpose processors. Innovative and efficient object detection and posture tracking techniques enable the analysis of images and/or video recordings captured by one or more on-device cameras to determine user or player analytics including movement patterns, body postures, and optionally other non-human objects such as balls present in the training area. In various embodiments, computer vision techniques such as image registration, motion detection, background subtraction, objection tracking, 3D-reconstruction techniques, cluster analysis techniques, camera calibration techniques such as camera pose estimation and sensor fusion, and modern machine learning techniques such as convolutional neural network (CNN), may be selectively combined to perform high accuracy analysis in real-time on the mobile device. The limited computational resources in a mobile device present a unique challenge. For instance, a smartphone's limited CPU processing power is heat-sensitive. A CPU clock rate may be reduced by the operating system (OS) whenever the phone heats up. Also, when a system consumes too much memory, the system or application running on the system may be terminated by the OS. In some embodiments, the amount of battery that the virtual coaching system consumes is controlled, otherwise the limited battery on a smartphone may not last a given duration (e.g., duration of a whole training session).

Another key feature in this virtual coaching and performance training process is the simulation of external stimuli and the facilitation of user response or interaction through a user interface to complete some aspects of the physical training. An in-person partner or coach can provide instructions for a next set of drills, and often serves as an assistant in clocking time, providing targets and challenges, and giving changing orders at random time instances to train a player's reaction time. Embodiments of the present invention can simulate such external stimuli and track the player's physical reactions in response. That is, while the process of capturing a training video is passive without explicit user inputs, interactive virtual coaching and performance training involve active user interaction with an augmented virtual environment, through particular posture sequences and/or audio inputs, but without the use of wearable sensors or controls. For example, a user or player may be required to jump to a certain height for a given number of times to achieve a training goal. The desired height may be simulated as a virtual target line superimposed onto the training video, and interactivity may derive from the player trying to virtually touch the line with his hand or top of his head in the image plane of the training video.

Similarly, other forms of external stimulation may be generated by embodiments of the present invention, including target objects and goals. Examples include but are not limited to, images indicative of certain movements, such as blocking movements in the game of basketball, noise effects similar to the sounds generated by a crowd of observers, and the like. Such external stimuli, goal, or cue may be designed to adjust a difficulty level of the training session, to tailor embodiments of the present invention to all skill levels, from beginner through advanced.

In another aspect, embodiments of the virtual coaching and training system as disclosed herein relate to monitoring a training exercise using the mobile computing device, determining various player analytics, performance metrics, or statistics, and tracking of such data over time to generate a historical database, thereby allowing for player performance tracking over time. This and various other aspects of the disclosure may further serve as a virtual coach for users in extracting statistics associated with various performed tasks and activities, presenting historical trends, and providing feedback for the players to improve their skills.

In general, the term analytics refers to meaningful patterns, knowledges, and information from data or statistics. In this disclosure, user or player analytics refer to quantitative and qualitative characterizations of player actions during one or more training sessions. For example, for a ball sport game, player analytics include but are not limited to, shot types, shot make/miss, shot score, player movement patterns, player moving speed, moving direction, reaction time, jump height and type, jump foot, landing foot, shot release time and angle, and posture statistics such as body bend angle, body rotation, leg bend ratio, and leg power. An analytic may be both a shot analytic specific to a given shot attempt, and a player analytic specific to an identified player. In addition, game analytics generally refers to statistical analytics generated from player analytics and optionally shot analytics over the duration of a game, and team analytics refers to analytics aggregated across players of a team.

Player analytics or metrics are specific to different types of sports. In an illustrative basketball dribbling training example, one or more users may be able to perform a dribbling workout, and an application on a mobile computing device implementing an embodiment of the present invention may be configured to monitor the dribbling workout to determine dribble speed, dribble accuracy, ability of the user to make specific movements during dribbling, combinations thereof, and/or the like.

As noted, the physical activities and sports being trained for include traditional physical games played in the real world, such as on a court, field, trail, and the like. Interactivity with the virtual world provides training opportunities for specific skills and techniques. In some embodiments, another level of interactivity may exist among one or more users linked through a network, where multiple users or players may train together at the same time, and training results may be compared across time.

Exemplary Embodiment for Virtual Coaching and Training for Body-Eye Coordination As an illustrative embodiment, FIGS. 1A to 1D show respective setup and architectural overview of a NEX system for virtual coaching and performance training in body-eye coordination and reaction time for basketball dribbling.

FIG. 1A is an exemplary setup 100 for enabling interactive virtual coaching and performance training with a mobile computing device, according to some embodiments of the present invention. A user or player 110 trains in front of a mobile computing device 115 secured on a mounting apparatus. The optional mounting apparatus may be a tripod or a kickstand. During a training session, an embodiment of the NEX system implemented on mobile computing device 115 may provide audio or visual instructions, goals, or cues, for user 110 to perform a next movement or set of movements. Mobile computing device 115 may comprise one or more cameras for capturing a training video of user 110, for example using a front-facing camera, for computer vision-based, real-time, near real-time, or off-line posture analysis. The captured training video may be presented to the user through a display screen on the mobile computing device, with or without superimposed graphical or textual instructions, cues, analytics, statistics, or other visual training information add-ons. In some embodiments, mobile computing device 115 may be coupled to a larger external display, through a wireless or wired connection, such that the user may see the captured training video and optional training information with better clarity.

Figure 1B:
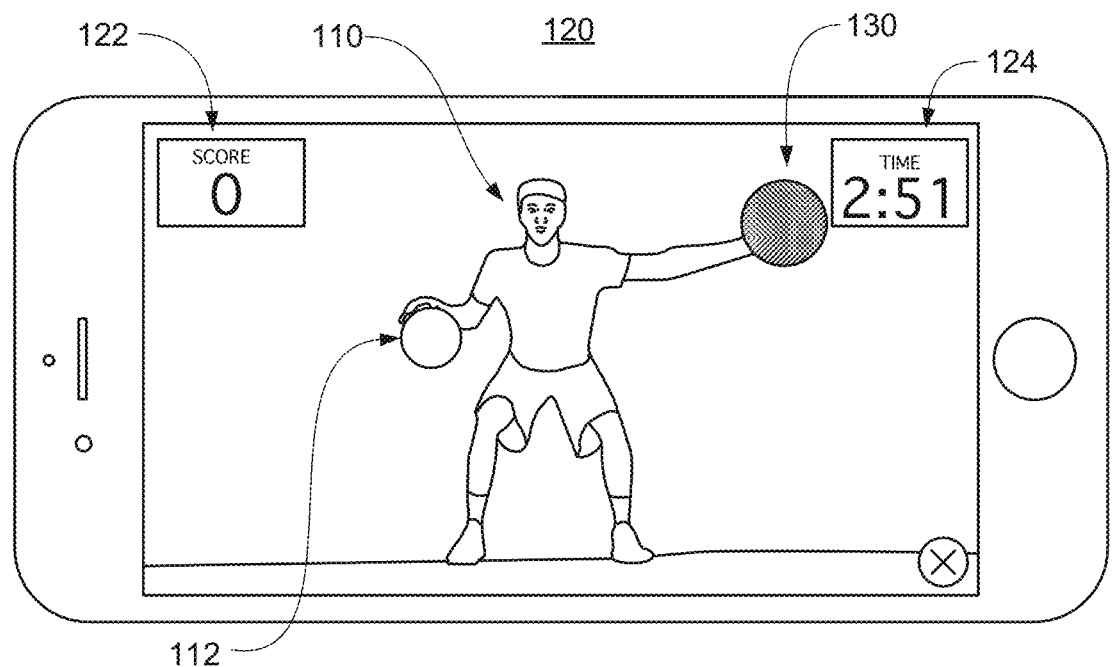
FIGS. 1B and 1C show respective diagrams representing an exemplary application running on the mobile computing device in FIG. 1A, while the user performs a training activity, according to some embodiments of the present invention.
Figure 1C:
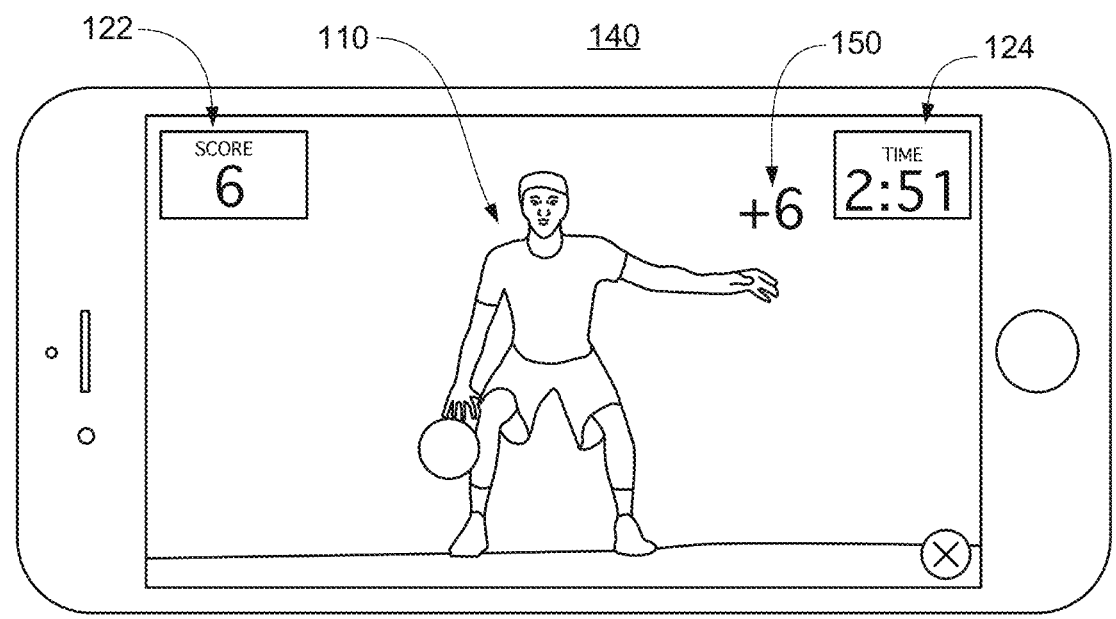

Correspondingly, FIGS. 1B and 1C show respective diagrams 120 and 140 of an exemplary application running on the mobile computing device 115 in FIG. 1A, while the user performs a dribble training activity, according to some embodiments of the present invention. While user 110 is dribbling ball 112, a visual cue 130 appears on the screen at a random location as generated by the NEX system for user 110 to touch with his non-dribbling hand. Visual cue 130 is presented for a cue period, which may have a pre-determined duration, or may terminate once it is determined that the player has touched visual cue 130. Depending on how fast the player touches cue 130 from when cue 130 first appears, a point score 150 may be given by the NEX system, displayed to user 110 as a feedback, and be added to a total score 122. If user 110 does not touch visual cue 130 successfully within the pre-determined cue period, a zero point score may be given. In some embodiments, a training period of three minutes may be counted down through a timer 124.

In this basketball training example, a baseline training activity of ball dribbling is required, whereby the user tries to hit cue targets presented to the user at the user device with his non-dribbling hand as the targets appear on the display. Points may be awarded to the user whenever the user successfully virtually touches a given target without stopping the dribbling activity. Further, more points may be awarded to the user for virtually touching the targets quicker while dribbling. In some embodiments, a termination symbol such as an "X" may be displayed to allow the user to abort the training session.

In various embodiments, the interactive and reactionary nature of a digital virtual workout may serve to address various deficiencies of training without the benefit of a partner or coach, which may further allow users to practice in a way that more effectively translates to game situations. In one embodiment, altering the scope of the user's attention, for example, having the user concentrate on targets rather than on dribbling dynamics, may serve to better mimic one or more game-like situations, such as surveying the floor while dribbling. Further, in various embodiments, the graphical user interface (GUI) presented to the user at the user device may be relatively simple, have familiar elements of design, and may represent a futuristic approach to displaying such analyses and providing feedback and training routines.

Figure 1D:
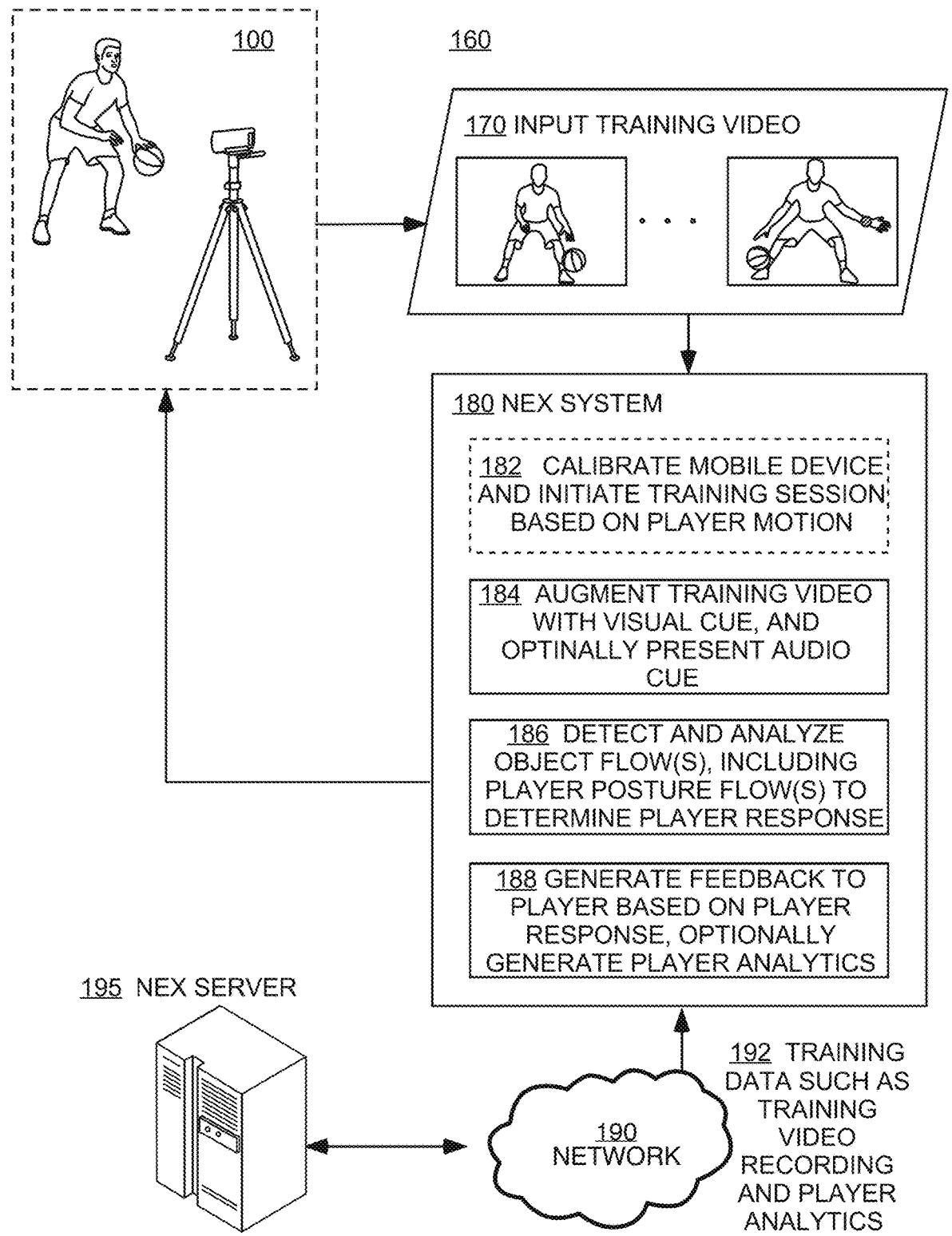
FIG. 1D is an architectural overview of a mobile computing device-based system for interactive virtual coaching and training, according to some embodiments of the present invention.

FIG. 1D is an architectural overview 160 of a mobile computing device-based system for interactive virtual coaching and performance training, according to some embodiments of the present invention. A NEX system 180 shown in FIG. 1D may be implemented on mobile device such as 115 to capture player actions in a game area. An input training video 170 thus captured by mobile computing device 115 is analyzed by NEX system 180 using one or more computer vision algorithms, which may also be implemented on mobile computing device 115. Player motion, movement, or posture, and optionally training objects present in the video may be analyzed at a step 182 to initiate the training session, after the mobile computing device or the captured training video has been calibrated or adjusted for levelness, distance from the player, brightness under a current lighting condition, and other similar environmental parameters. Next, the training video may be augmented with a visual cue, where a graphical or textual symbol is superimposed onto the training video, at a step 184. At step 186, player posture flows and object flows may be further detected and analyzed, to determine how the player has responded to the presented visual cue. In this particular example, a player is prompted to virtually touch the visual cue with his or her non-dribbling hand. Based on user responses determined through the user's posture flow, NEX system 180 generates a feedback to the user at a step 188, and optionally generate one or more player analytics. In some embodiments, training data 192 from one or more other players, such as training video recordings and player analytics, may be downloaded from a NEX server 195 via a network 190. While not shown explicitly here, NEX server 195 may comprise one or more databases for storing training videos and player analytics, and one or more processors for generating live or historical training statistics for participating users. Exemplary implementations for NEX server 195 are provided with reference to FIG. 3.

In some embodiments, a convolutional neural network (CNN) may be applied to some or all frames of training video 170 to detect game objects such as basketballs and hockey pucks, as well as individual players and their postures. A tracking algorithm may be performed to track all detected balls and postures, where multiple balls or players may be present in each frame of the shot attempt video, to generate multiple ball flows and posture flows. In some embodiments, a flow refers to object instances from different frames. All object instances in the same flow may be considered the same object. In other words, for a ball or posture in a flow, all instances of the ball or posture in all frames of the video are identified as the same object. In various embodiments, object clustering or classification methods such as k-means, affinity propagation, density-based spatial clustering of applications with noise (DB-SCAN) and/or k-nearest neighbors (KNN) may be applied to differentiate detected player images into multiple players.

When a single player is being recorded, a single posture flow may be detected and associated with the player directly. When multiple players are being recorded, NEX system 180 may distinguish the players based on visual features such as jersey colors, or distinguishing facial or body features, and each player may register with NEX system 180 before the start of the training session by logging in such visual features. For example, in a single-device, multi-player, "2-player reaction" training session, the camera on the mobile computing device may capture sufficient training area to allow two players to train together, where the two players compete in responding to the visual cue. In the case where the player competes in virtually touching the visual cue, the player who virtually touches the visual cue first may be rewarded a positive point score, similar to the single-player case.

To detect objects of interests such as court lines, balls and players from frames of the input video, one or more convolutional neural networks (CNN) may be applied. Each CNN module may be trained using one or more prior input videos. A CNN utilizes the process of convolution to capture the spatial and temporal dependencies in an image, and to extract features from the input video for object detection. Feature extraction in turn enables segmentation or identification of image areas representing these objects such as balls and players, and further analysis to determine player body postures. A ball moves through space, leading to changing size and location from video frame to video frame. A player also moves through space while handling the ball, leading to both changing locations, sizes, and body postures.

In computer vision, pose or posture estimation is the task of identifying or detecting the position and orientation of an object in an image, relative to some coordinate system. This is generally formulated as the process of determining key point locations that describe the object. In the case of a ball, pose estimation may refer to determining the center and radius of the ball in the image plane. Hand pose estimation, on the other hand, is the process of determining finger joints and fingertips in a given image, where the whole hand is viewed as one object. Head pose estimation is the process of determining and analyzing facial features to obtain the 3D orientation of human head with respect to some reference point. Human pose estimation is the process of detecting major parts and joints of the body, such as head, torso, shoulder, ankle, knee, and wrist. In this disclosure, a "player image" refers to the image of a human player segmented from the input video, for example as defined by a bounding box; "posture" and "pose" are used interchangeably to refer to either a player image or a set of key points extracted from the player image to represent body pose or posture. In addition, instead of only determining whether an object such as a ball or a player is present in a given video frame, object detection or extraction in the present disclosure refers to determining the relative position, size, and/or pose of a ball, player, or other entities of interest.

Once objects are detected or extracted from individual frames, object flows may be established by grouping detected objects along a timeline. Object movements across frames are continuous in the sense that object locations can only change in small increments from one video frame to the next. Thus, detected objects may be grouped based on location information into one or more object flows. For example, object flows may be established by computing a matching score for each object and existing object flow combination, and assigning objects to existing object flows with the highest matching score. At the beginning when no object flows yet exist, an initialization process may be performed based on an initial collection of a small number of objects, detected with high accuracy. In addition, a new flow may be created if the detected object does not match to any existing flows with a high score.

Implementation Using Computer Program Products, Methods, and Computing Entities

Exemplary System Architecture

Figure 2:
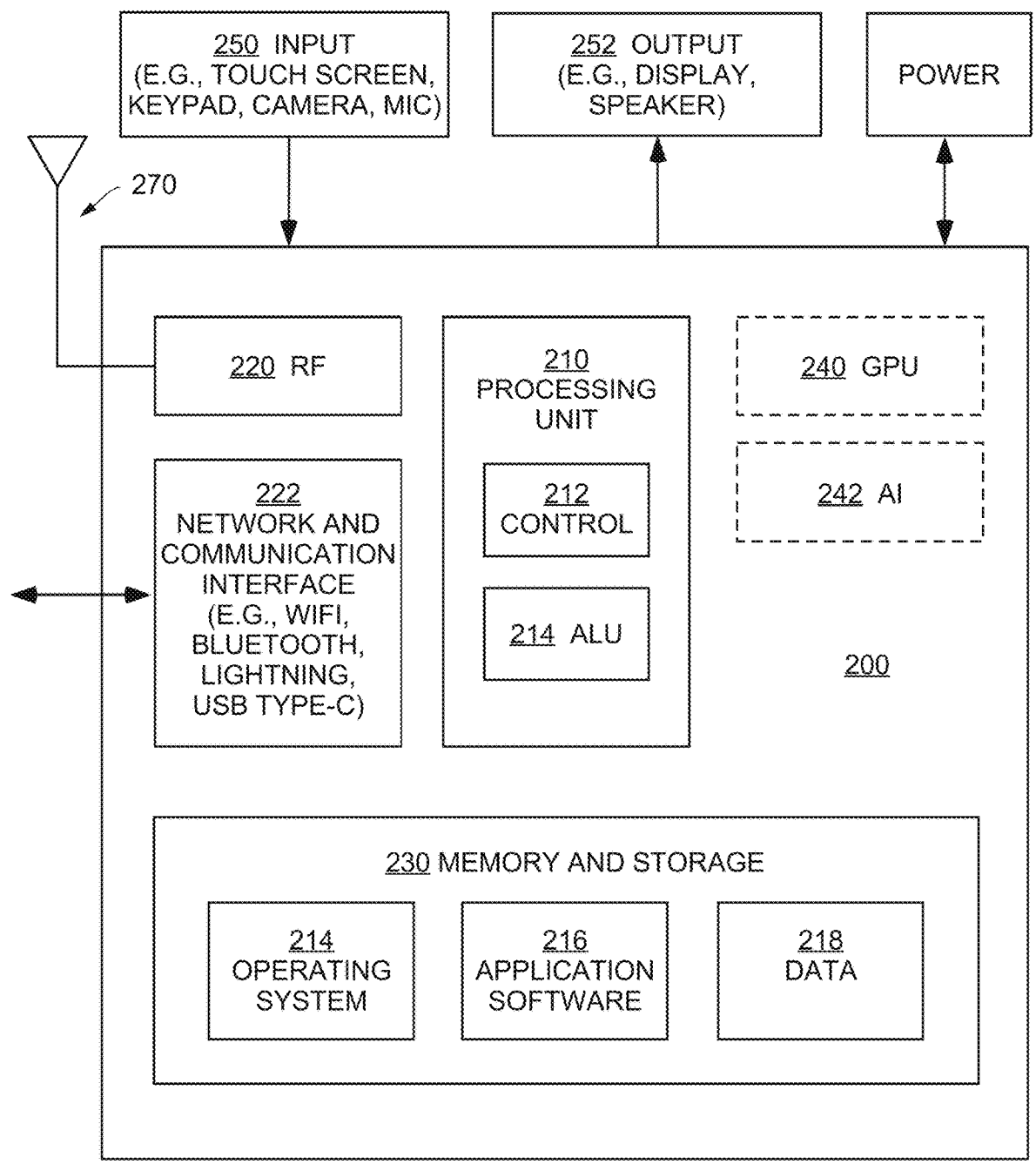
FIG. 2 is an exemplary schematic diagram of a user computing entity for implementing an interactive virtual coaching and training system, according to exemplary embodiments of the present invention.
Figure 3:
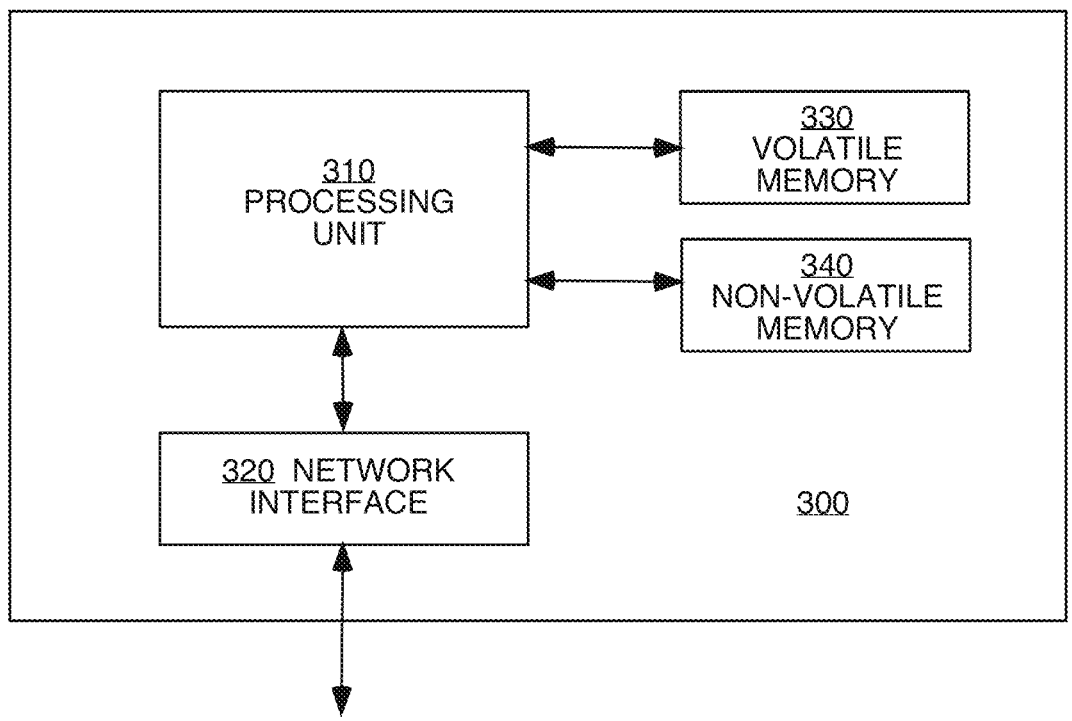
FIG. 3 is an exemplary schematic diagram of a management computing entity for implementing an interactive virtual coaching and training system, according to exemplary embodiments of the present invention.

An exemplary embodiment of the present disclosure may include one or more user computing entities 200, one or more networks, and one or more server or management computing entities 300, as shown in FIGS. 2 and 3. Each of these components, entities, devices, systems, and similar words used herein interchangeably may be in direct or indirect communication with, for example, one another over the same or different wired or wireless networks. Additionally, while FIGS. 2 and 3 illustrate the various system entities as separate, standalone entities, the various embodiments are not limited to this particular architecture.

Exemplary User Computing Entity

FIG. 2 is an exemplary schematic diagram of a user computing device for implementing a virtual coaching and performance training system, according to exemplary embodiments of the present invention. A user operates a user computing device 200 that includes one or more components as shown. As will be recognized, these architectures and descriptions are provided for exemplary purposes only and are not limiting to the various embodiments.

In general, the terms device, system, computing entity, entity, and/or similar words used herein interchangeably may refer to, for example, one or more computers, computing entities, desktops, mobile phones, tablets, phablets, notebooks, laptops, distributed systems, gaming consoles (e.g., Xbox, Play Station, Wii), watches, glasses, key fobs, radio frequency identification (RFID) tags, ear pieces, scanners, cameras, wristbands, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, retrieving, operating on, processing, displaying, storing, determining, creating, generating, generating for display, monitoring, evaluating, comparing, and/or similar terms used herein interchangeably. In various embodiments, these functions, operations, and/or processes can be performed on data, content, information, and/or similar terms used herein interchangeably. Furthermore, in embodiments of the present invention, user computing device 200 may be a mobile device, and may be operated by a user participating in an interactive physical training activity. On the other hand, a NEX server 195 may be implemented according to the exemplary schematic diagram shown in FIG. 3, possibly in the cloud, and possibly with logically or physically distributed architectures.

As shown in FIG. 2, the user computing entity 200 may include an antenna 270, a radio transceiver 220, and a processing unit 210 that provides signals to and receives signals from the transceiver. The signals provided to and received from the transceiver may include signaling information in accordance with air interface standards of applicable wireless systems. In this regard, the user computing entity 200 may be capable of operating with one or more air interface standards, communication protocols, modulation types, and access types. More particularly, the user computing entity 200 may operate in accordance with any of a number of wireless communication standards and protocols. In some embodiments, user computing entity 200 may operate in accordance with multiple wireless communication standards and protocols, such as 5G, UMTS, FDM, OFDM, TDM, TDMA, E-TDMA, GPRS, extended GPRS, CDMA, CDMA2000, 1xRTT, WCDMA, TD-SCDMA, GSM, LTE, LTE advanced, EDGE, E-UTRAN, EVDO, HSPA, HSDPA, MDM, DMT, Wi-Fi, Wi-Fi Direct, WiMAX, UWB, IR, NFC, ZigBee, Wibree, Bluetooth, and/or the like. Similarly, the user computing entity 200 may operate in accordance with multiple wired communication standards and protocols, via a network and communication interface 222.

Via these communication standards and protocols, the user computing entity 200 can communicate with various other computing entities using concepts such as Unstructured Supplementary Service Data (USSD), Short Message Service (SMS), Multimedia Messaging Service (MMS), Dual-Tone Multi-Frequency Signaling (DTMF), and/or Subscriber Identity Module Dialer (SIM dialer). User computing entity 200 can also download changes, add-ons, and updates, for instance, to its firmware, software (e.g., including executable instructions, applications, program modules), and operating system.

In some implementations, processing unit 210 may be embodied in several different ways. For example, processing unit 210 may be embodied as one or more complex programmable logic devices (CPLDs), microprocessors, multi-core processors, coprocessing entities, application-specific instruction-set processors (ASIPs), microcontrollers, and/or controllers. Further, the processing unit may be embodied as one or more other processing devices or circuitry. The term circuitry may refer to an entirely hardware embodiment or a combination of hardware and computer program products. Thus, processing unit 210 may be embodied as integrated circuits, application specific integrated circuits (ASICs), field programmable gate arrays (FPGAs), programmable logic arrays (PLAs), hardware accelerators, other circuitry, and/or the like. As will therefore be understood, processing unit 210 may be configured for a particular use or configured to execute instructions stored in volatile or non-volatile media or otherwise accessible to the processing unit. As such, whether configured by hardware or computer program products, or by a combination thereof, processing unit 210 may be capable of performing steps or operations according to embodiments of the present invention when configured accordingly.

In some embodiments, processing unit 210 may comprise a control unit 212 and a dedicated arithmetic logic unit 214 (ALU) to perform arithmetic and logic operations. In some embodiments, user computing entity 200 may optionally comprise a graphics processing unit 240 (GPU) for specialized image and video rendering tasks, and/or an artificial intelligence (AI) accelerator 242, specialized for applications including artificial neural networks, machine vision, and machine learning. In some embodiments, processing unit 210 may be coupled with GPU 240 and/or AI accelerator 242 to distribute and coordinate processing tasks.

In some embodiments, user computing entity 200 may include a user interface, comprising an input interface 250 and an output interface 252, each coupled to processing unit 210. User input interface 250 may comprise any of a number of devices or interfaces allowing the user computing entity 200 to receive data, such as a keypad (hard or soft), a touch display, a mic for voice/speech, and a camera for motion or posture interfaces. User output interface 252 may comprise any of a number of devices or interfaces allowing user computing entity 200 to provide information to a user, such as through the touch display, or a speaker for audio outputs. In some embodiments, output interface 252 may connect user computing entity 200 to an external loudspeaker or projector, for audio or visual output.

User computing entity 200 may also include volatile and/or non-volatile storage or memory 230, which can be embedded and/or may be removable. A non-volatile memory may be ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. The volatile and non-volatile storage or memory may store an operating system 214, application software 216, data 218, databases, database instances, database management systems, programs, program modules, scripts, source code, object code, byte code, compiled code, interpreted code, machine code, executable instructions, and/or the like to implement the functions of user computing entity 200. As indicated, this may include a user application that is resident on the entity or accessible through a browser or other user interface for communicating with a management computing entity and/or various other computing entities.

In some embodiments, user computing entity 200 may include location determining aspects, devices, modules, functionalities, and/or similar words used herein interchangeably. For example, user computing entity 200 may include outdoor positioning aspects, such as a location module adapted to acquire, for example, latitude, longitude, altitude, geocode, course, direction, heading, speed, universal time (UTC), date, and/or various other information/data. In one embodiment, the location module may acquire data, sometimes known as ephemeris data, by identifying the number of satellites in view and the relative positions of those satellites. Alternatively, the location information may be determined by triangulating the user computing entity's position in connection with a variety of other systems, including cellular towers, Wi-Fi access points, and/or the like. Similarly, user computing entity 200 may include indoor positioning aspects, such as a location module adapted to acquire, for example, latitude, longitude, altitude, geocode, course, direction, heading, speed, time, date, and/ or various other information/data. Some of the indoor systems may use various position or location technologies including RFID tags, indoor beacons or transmitters, Wi-Fi access points, cellular towers, nearby computing devices (e.g., smartphones, laptops) and/or the like. For instance, such technologies may include the iBeacons, Gimbal proximity beacons, Bluetooth Low Energy (BLE) transmitters, NFC transmitters, and/or the like. These indoor positioning aspects can be used in a variety of settings to determine the location of someone or something to within inches or centimeters.

In an interactive physical training session, a user computing entity 200 may be deployed (e.g., installed; configured; accepted; installed and accepted; configured and accepted; installed, configured, and accepted; or the like) in a training area that includes players and/or game equipment. In some embodiments, at least one input device on user computing entity 200 may collect or may be configured to collect information (e.g., data, metadata, and/or signaling) indicative of operational features of the training area and/or equipment for analysis by processing unit 210. For example, computer vision algorithms as implemented on user computer entity 200 may be configured to detect the location of court lines, field boundaries, one or more balls, or goal posts in an input video as captured by an input camera device.

In some embodiments, a system for virtual coaching and performance training may include at least one user computing device such as a mobile computing device and optionally a mounting apparatus for the at least one mobile computing device. The mounting apparatus may be a tripod or a kickstand, and may mount the electronic device with a camera of the user computing device positioned to monitor a training area. In some embodiments, the user computing device may be hand-held or put on the ground leaning against certain articles such as a water bottle. In some embodiments, the system for virtual coaching and performance training further comprises a sound device, for example, earbuds (e.g., wireless earbuds) or a speaker system (e.g., a public address (PA) system) coupled to the at least one user computing device. The sound device may serve to provide instruction and feedback regarding the training session to the user. In some embodiments, the system optionally comprises an optical device such as a projector, a projection lamp, a laser pointing system, a jumbotron, a television screen, or the like, that can facilitate an interactive training session. For example, a laser pointing system may point to a location in the training area to direct the user to position himself or herself, or it may point to a location in a display of the training video as the visual cue, to direct the user to perform a desired set of physical movements.

In some embodiments, user computing entity 200 may communicate to external devices like other smartphones and/or access points to receive information such as software or firmware, or to send information (e.g., training data such as analytics, statistics, scores, recorded video, etc.) from the memory of the user computing device to external systems or devices such as servers, computers, smartphones, and the like.

In some embodiments, two or more users may establish a connection between their computing devices using a network utilizing any of the networking protocols listed previously. At least two of the users may be in geographically different training areas. In some embodiments, the user computing devices may use a network interface such as 222 to communicate with various other computing entities, such as by communicating data, content, information, and/or similar terms used herein interchangeably that can be transmitted, received, operated on, processed, displayed, stored, and/or the like.

In some embodiments, data such as training statistics, scores, and videos may be uploaded by one or more user computing devices to a server such as shown in FIG. 3 when the device accesses a network connection, such as a wireless access point or hotspot. The data transfer may be performed using protocols like file transfer protocol (FTP), MQ telemetry transport (MQTT), advanced message queuing protocol (AMQP), hypertext transfer protocol (HTTP), and HTTP secure (HTTPS). These protocols may be made secure over transport layer security (TLS) and/or secure sockets layer (SSL).

In some embodiments, audio generated by a user computing device and/or audio generated by one or more users may be used to facilitate an interactive training session. In some embodiments, audio may be used to (i) direct users to particular positions on training areas (with further audio feedback to help the users locate themselves more accurately), (ii) inform users about a motion or action that a user needs to do as part of the training (e.g., shoot a ball at a basket, perform a back flip, perform an exercise such as pushups, and the like), (iii) provide feedback to the user (e.g., to inform them if the users are making a wrong move, running out of time, have successfully completed a given drill, or achieved a particular score), or (iv) report on the progress of the training session (statistics, leaderboard, and the like). In some embodiments, speech recognition and corresponding responses (e.g., audio, visual, textual, etc. responses) may also be used to facilitate the training session by allowing users to set options, correct mistakes, or start or stop the training session.

In some embodiments, artificial intelligence-based computer vision algorithms may be used to perform at least one of the following: (i) ensure that users are located where they should be, (ii) determine when/if users successfully complete a task, (iii) rank the quality of users' motion/action, and (iv) award quality points or other attributes depending on the nature of the users' motion (e.g., in a game of basketball, determining whether a user scored by dunking or by performing a layup).

In various embodiments, during the physical activities performed by users, the mobile computing device may not be on the user's person, and instructions may be given via a speaker or other remote devices connected to the mobile device. Further, computer vision algorithms may be used on the mobile device to guide and monitor training being conducted within the mobile device camera's field of view. Accordingly, embodiments of devices described herein can employ artificial intelligence (AI) to facilitate automating one or more training features of functionalities as described herein.

To provide for or aid in the numerous determinations (e.g., determine, ascertain, infer, calculate, predict, prognose, estimate, derive, forecast, detect, compute) of training settings, player postures and player analytics described herein, components described herein may examine the entirety or a subset of data to which it is granted access and can provide for reasoning about or determine states of the system or environment from a set of observations as captured via events and/or data. Determinations may be employed to identify a specific context or action, or may generate a probability distribution over states, for example. The determinations may be probabilistic. That is, the computation of a probability distribution over states of interest based on a consideration of data and events. Determinations may also refer to techniques employed for composing higher-level events from a set of events and/or data.

Such determinations may result in the construction of new events or actions from a set of observed events and/or stored event data, whether the events are correlated in close temporal proximity, and whether the events and data come from one or several event and data sources. For example, training instructions and feedbacks to player may be generated from one or more player analytics derived from user training actions. Further, components disclosed herein may employ various classification schemes (e.g., explicitly trained via training data or implicitly trained via observing behavior, preferences, historical information, receiving extrinsic information, etc.) and/or systems (e.g., support vector machines, neural networks, expert systems, Bayesian belief networks, fuzzy logic, data fusion engines, etc.) in connection with performing automatic and/or determined action in connection with the claimed subject matter. Thus, classification schemes and/or systems may be used to automatically learn and perform a number of functions, actions, and/or determinations.

Exemplary Management Computing Entity

FIG. 3 is an exemplary schematic diagram of a management computing entity 300, such as NEX server 195, for implementing a virtual coaching and performance training system, according to exemplary embodiments of the present invention. The terms computing entity, computer, entity, device, system, and/or similar words used herein interchangeably are explained in detail with reference to user computing entity 200.

As indicated, in one embodiment, management computing entity 300 may include one or more network or communications interface 320 for communicating with various computing entities, such as by communicating data, content, information, and/or similar terms used herein interchangeably that can be transmitted, received, operated on, processed, displayed, stored, and/or the like. For instance, management computing entity 300 may communicate with the user computing device 200 and/or a variety of other computing entities. Network or communications interface 320 may utilize a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, management computing entity 300 may be configured to communicate via wireless external communication networks using any of a variety of standards and protocols as discussed with reference to user computing device 200.

As shown in FIG. 3, in one embodiment, management computing entity 300 may include or be in communication with one or more processing unit 310 (also referred to as processors, processing circuitry, processing element, and/or similar terms used herein interchangeably) that communicate with other elements within the management computing entity 300. As will be understood, processing unit 310 may be embodied in a number of different ways. For example, as one or more CPLDs, microprocessors, multi-core processors, coprocessing entities, ASIPs, microcontrollers, and/or controllers, in the form of integrated circuits, application specific integrated circuits (ASICs), field programmable gate arrays (FPGAs), programmable logic arrays (PLAs), hardware accelerators, other circuitry, and/or the like. As will therefore be understood, processing unit 310 may be configured for a particular use or configured to execute instructions stored in volatile or non-volatile media 330 and 340. As such, whether configured by hardware or computer program products, or by a combination thereof, processing unit 310 may be capable of performing steps or operations according to embodiments of the present disclosure when configured accordingly.

Although not shown explicitly, management computing entity 300 may include or be in communication with one or more input elements, such as a keyboard, a mouse, a touch screen/display, a camera for motion and movement input, a mic for audio input, a joystick, and/or the like. Management computing entity 300 may also include or be in communication with one or more output elements such as speaker, screen/display, and/or the like.

In various embodiments, one or more of the components of management computing entity 300 may be located remotely from other management computing entity components, such as in a distributed system or in the cloud. Furthermore, one or more of the components may be combined and additional components performing functions described herein may be included in the management computing entity 300.

Machine Vision and Machine Learning Modules

As described herein, embodiments of the present invention use one or more artificial intelligence, machine vision, and machine learning algorithms or modules for analyzing training videos and facilitating interactive virtual coaching and performance training sessions. Various exemplary machine vision algorithms are within the scope of the present invention used for performing object recognition, gesture recognition, pose estimation, and so forth. The following description describes in detail some illustrative machine vision and machine learning algorithms for implementing some embodiments of the present invention.

Illustrative Machine Vision Architectures

Some exemplary machine vision algorithms utilize a deep learning network (DLN), for example a convolutional neural network (CNN). Neural networks are computer systems inspired by the human brain. They can be viewed as parallel, densely interconnected computational models that adaptively learn through automatic adjustment of system parameters based on training data. Input information are modified based on system parameters when traversing through layers of interconnected neurons or nodes, to activate or trigger particular outputs. The design of a neural network refers to the configuration of its architecture or topology, or the specific arrangements of layers and nodes in the network. The applicability, utility, and optimality of a neural network, and the framework in which the neural network is deployed are often mutually interdependent. Convolutional Neural Networks utilize the process of convolution to reduce the number of model parameters involved, while successfully capturing the spatial and temporal dependencies in an image.

Figure 4:
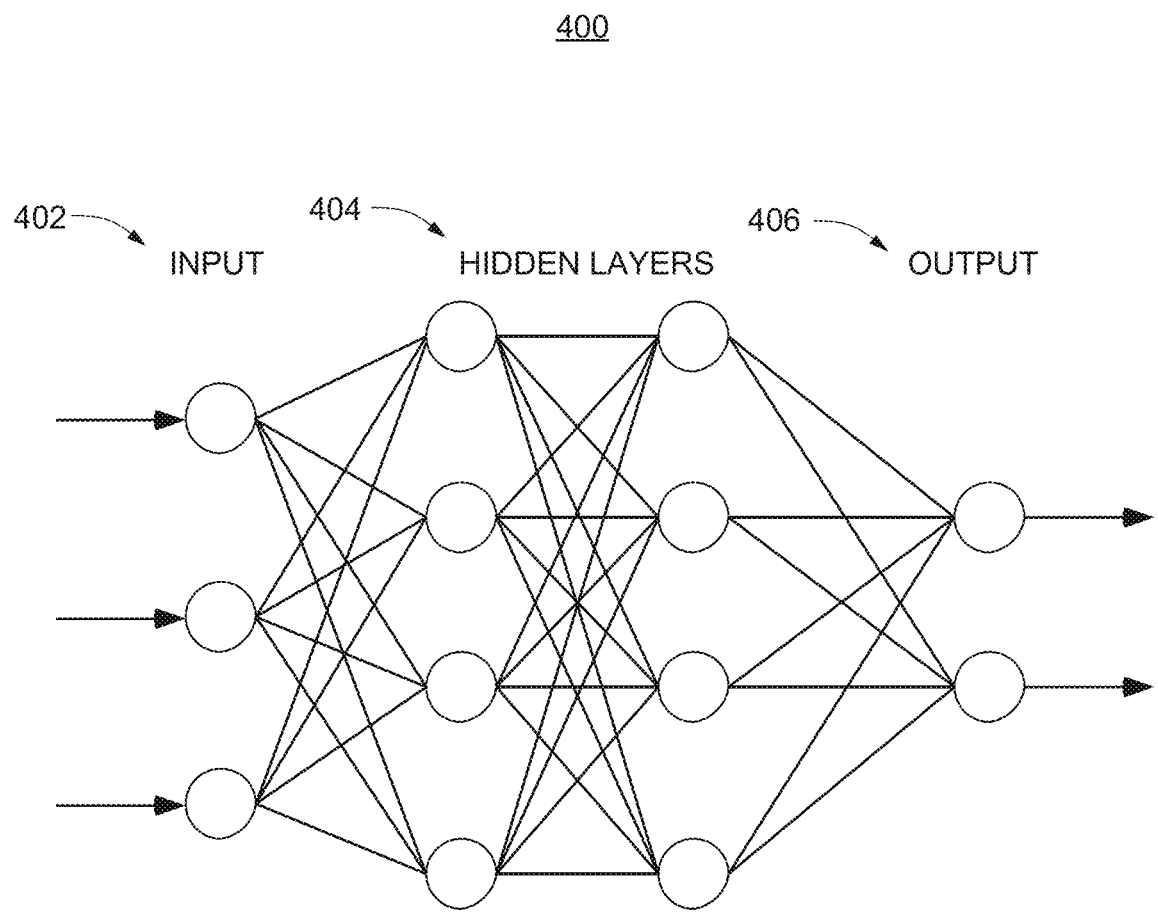
FIG. 4 shows an illustrative block diagram of a convolutional neural network (CNN) for image analysis, according to exemplary embodiments of the present invention.

More specifically, FIG. 4 shows an illustrative block diagram 400 of a convolutional neural network (CNN) for image analysis and object recognition, according to exemplary embodiments of the present invention. This exemplary CNN module 400 may be utilized for implementing various machine vision algorithms described herein. For example, it may be designed and trained to determine gestures and poses and other machine vision tasks required by the present invention, as would be recognized by one of ordinary skill in the art. An input layer 402 is connected via a multiplicity of hidden layers 404 to an output layer 406. Input layer 402 is a map for pixels of an input image. Exemplary hidden layers may include, but are not limited to, convolutional layers, Rectified Linear Units (ReLU), pooling layers, normalization layers, and fully connected layers. A convolutional layer applies a convolution or correlation operation by a kernel matrix to the input data to generate a feature map of the input image. ReLU is a non-linear activation function. Pooling layers reduce the dimensionality of the data to decrease the required computational power. A fully connected layer has full connections to all activations in the previous layer, and is needed before classification or output activation at output layer 406. Successive convolution-ReLU-pooling stages allow the successive extraction of low-level to high-level features, from edges, general shapes such as lines and circles, to specific shapes representing specific objects. FIG. 8A to 8E provide exemplary block diagrams of a detailed neural network design for pose estimation.

FIG. 4 shows only one illustrative CNN architecture that is within the scope of the present invention, but the present invention is not limited to the use of CNNs. Other machine vision algorithms are also within the scope of the present invention.

Illustrative Machine Learning Architectures

Figure 5:
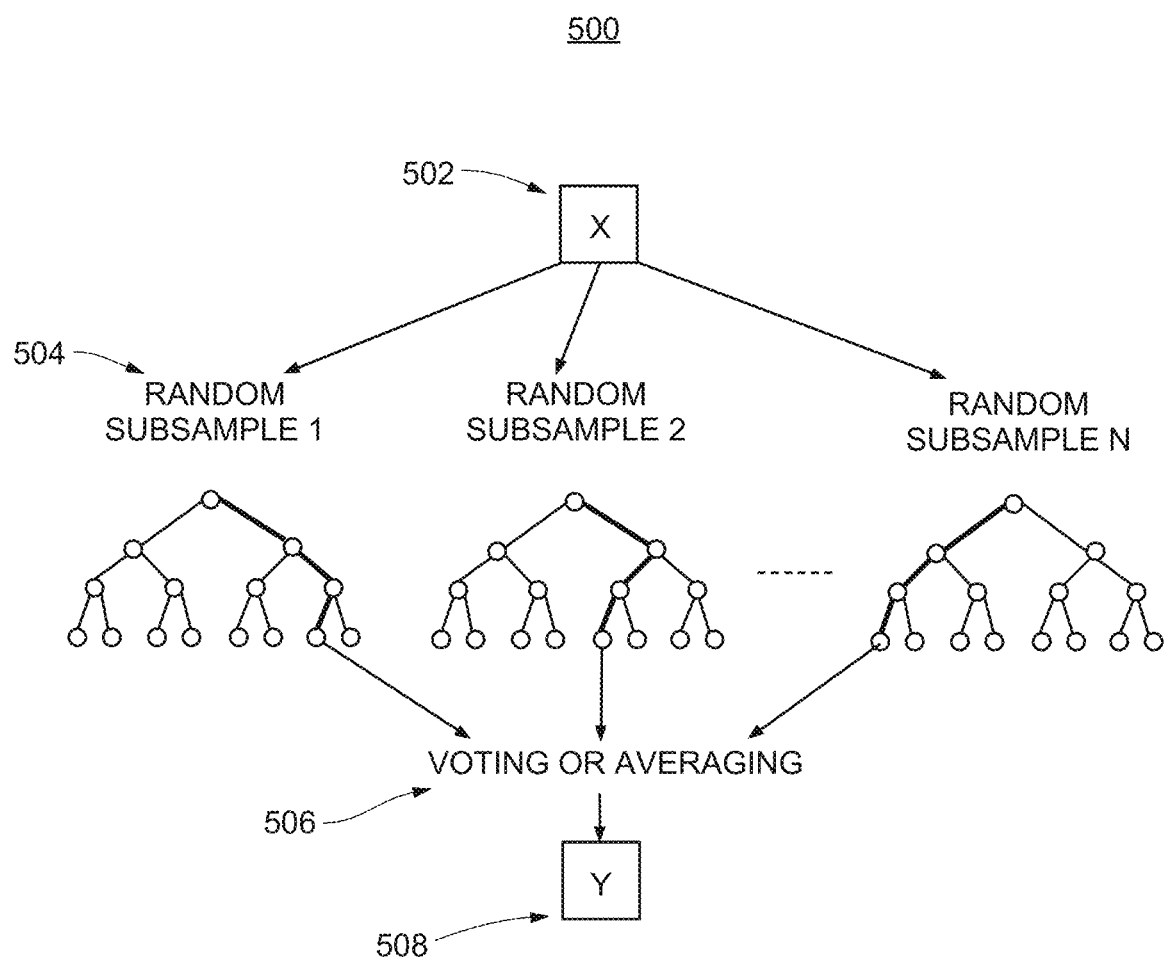
FIG. 5 shows an illustrative block diagram for a machine learning algorithm, according to exemplary embodiments of the present invention.

As states herein, various exemplary machine vision and machine learning algorithms are within the scope of the present invention for performing object recognition, gesture recognition, pose estimation, and so forth. FIG. 5 shows an illustrative block diagram 500 for a machine learning algorithm, according to exemplary embodiments of the present invention.

In particular, a supervised machine learning algorithm is shown, comprising an illustrative random forest algorithm. Random forest algorithms are a method for classification and regression. By using a multitude of decision tree predictors 504, each depending on the values of a random subset of a training data set 502, the chances of overfitting to the training data set may be minimized. The decision tree predictors are voted or averaged at a decision step 506 to obtain predictions 508 of the random forest algorithm. For the task of object recognition, input 502 to the machine learning algorithm may include feature values, while output 508 may include predicted gestures and/or poses associated with a user. Random forest is only one illustrative machine learning algorithm that is within the scope of the present invention, and the present invention is not limited to the use of random forest. Other machine learning algorithms, including but not limited to, nearest neighbor, decision trees, support vector machines (SVM), Adaboost, Bayesian networks, various neural networks including deep learning networks, evolutionary algorithms, and so forth, are within the scope of the present invention.

In short, embodiments of devices, systems, and their various components described herein may employ artificial intelligence (AI) to facilitate automating one or more functions described herein, including object recognition, gesture recognition, and pose estimation.

Training Machine Learning Algorithms

Figure 6:
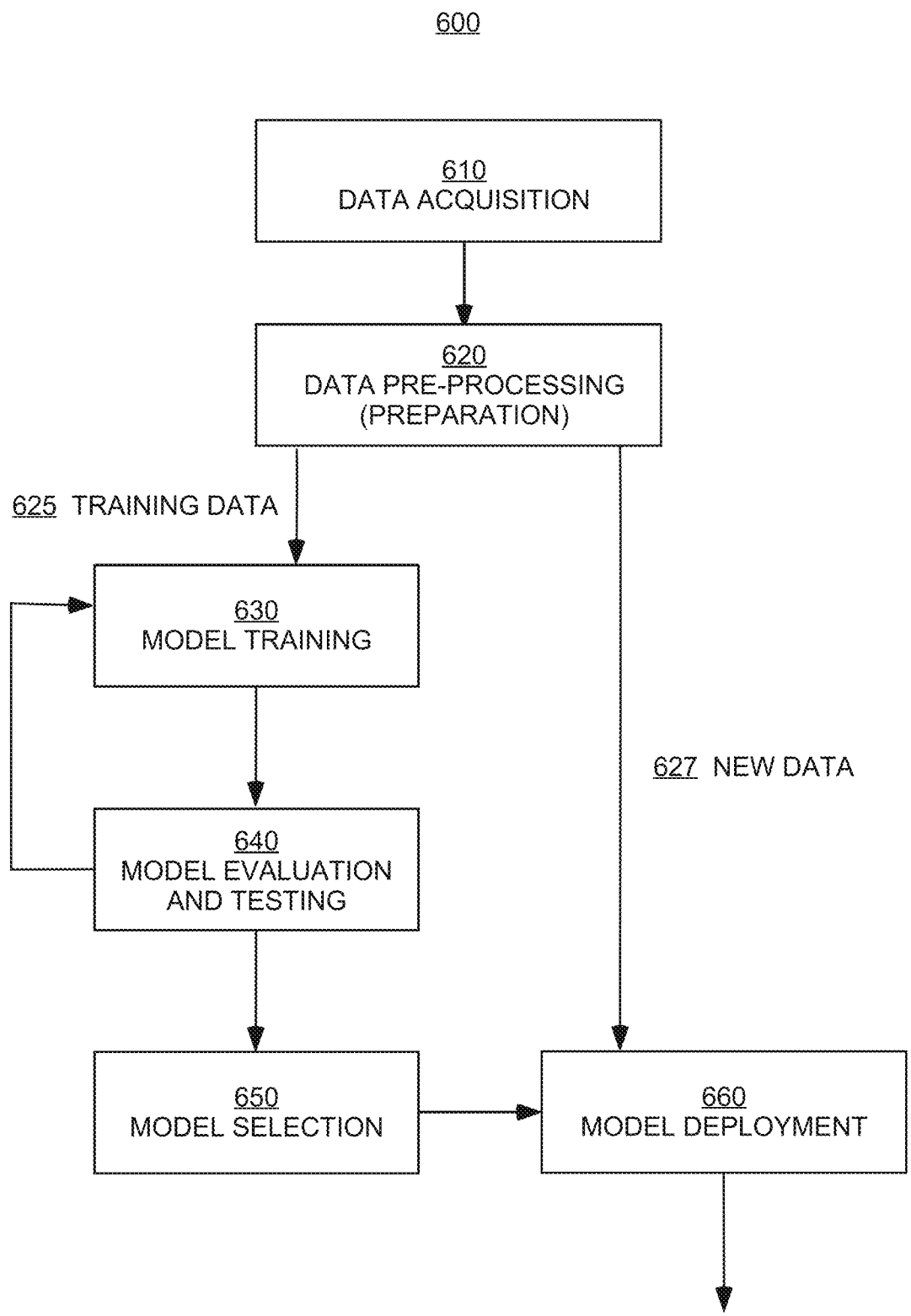
FIG. 6 shows an illustrative flow diagram for training a machine learning algorithm, according to exemplary embodiments of the present invention.

FIG. 6 shows an exemplary flow diagram 600 for training a machine learning (ML) algorithm, which may be utilized in object recognition, pose estimation, and object flow construction, according to exemplary embodiments of the present invention;

The training process begins at step 610 with data acquisition. At step 620, acquired data are pre-processed, or prepared. At step 630, a machine learning model is trained using training data 625. At step 640, the model is evaluated and tested, and further refinements to the model are fed back into step 630. At step 650, optimal model parameters are selected, for deployment at step 660. New data 627 may be used by the deployed model to make predictions.

A starting point for any machine learning method such as used by the machine learning component above is a documented dataset containing multiple instances of system inputs and correct outcomes (e.g., training data 625). This data set may be used, using methods known in the art, including but not limited to standardized machine learning methods such as parametric classification methods, non-parametric methods, decision tree learning, neural networks, methods combining both inductive and analytic learning, and modeling approaches such as regression models, to train the machine learning system and to evaluate and optimize the performance of the trained system. Thus, it would be understood by peoples of ordinary skill in the art that "training data" 625 as referred to in this subsection are directed to data for training a machine vision algorithm or a machine learning algorithm, while training data 192 refer to data collected from interactive training sessions. In some embodiments, training data 625 and training data 192 may comprise one or more overlapping components, such as recorded training videos.

The quality of the output of the machine learning system output depends on (a) pattern parameterization, (b) learning machine design, and (c) quality of the training database. These components may be refined and optimized using various methods. For example, the database may be refined by adding datasets for new documented gestures and poses. The quality of the database may be improved, for example, by populating the database with cases in which the gestures and/or poses were correctly recognized. In one embodiment, the database includes data, for example, of mistaken identification of gestures and/or poses, which may assist in the evaluation of a trained system.

Figure 7:
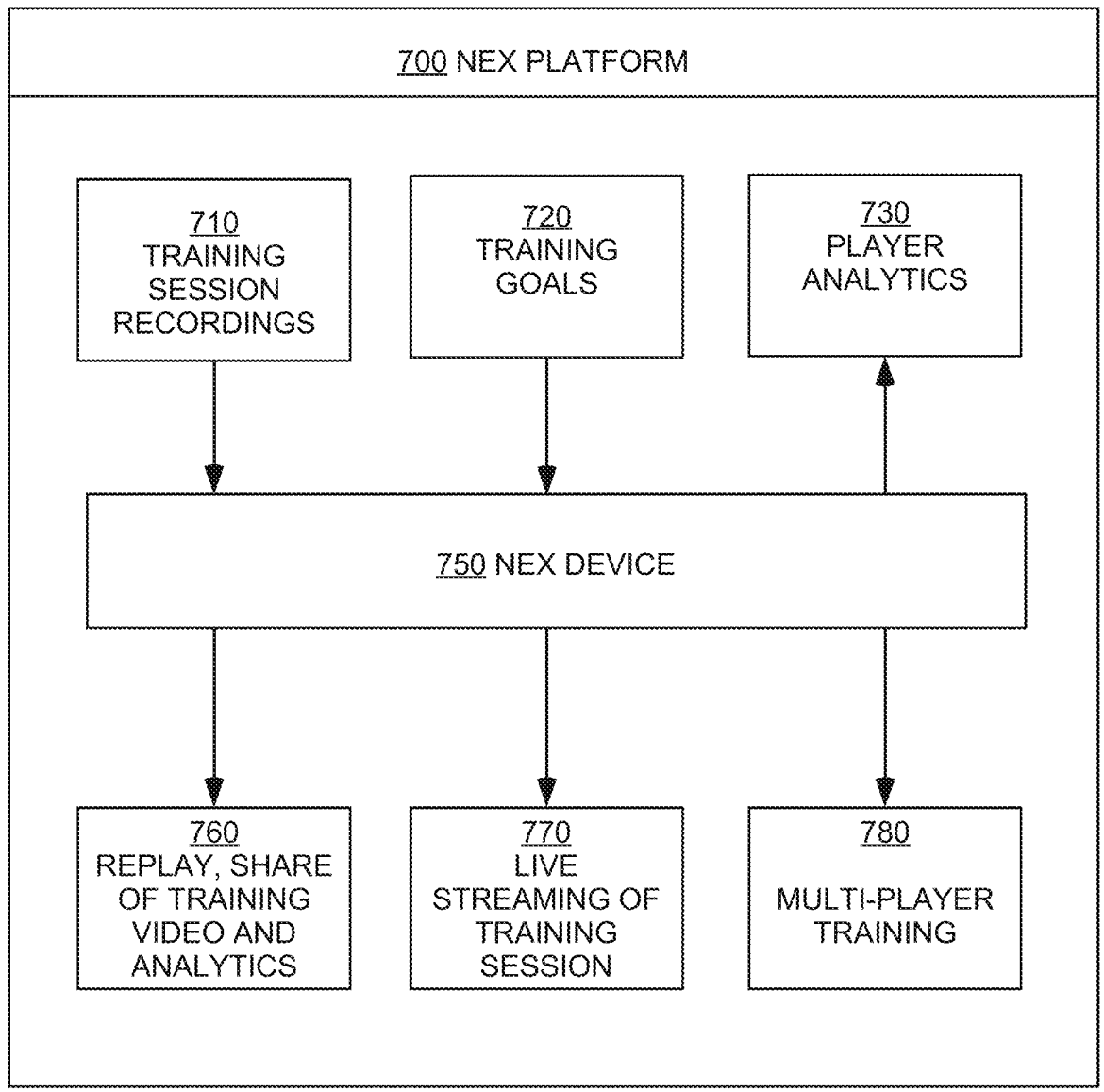
FIG. 7 is a schematic diagram illustrating an exemplary NEX platform, according to exemplary embodiments of the present invention.

FIG. 7 is a schematic diagram illustrating and summarizing some functionalities provided by an extended NEX platform 700, according to one embodiment of the present invention. In particular, a NEX device 750 may take in training goals 720, and facilitate different types of training activities, optionally generating player analytics 730, providing live streaming 770 of training sessions, and enable the replay and share 760 of training video and analytics. NEX platform 700 may also receive training session recordings 710, for local analysis to generate training analytics or statistics.

In some embodiments, NEX platform 700 also enables multi-player training processes 780, where multiple users located at the same or geographically different training areas may train at the same time or asynchronously, using a single mobile computing device or multiple mobile computing devices. Following are several exemplary embodiments for multi-player training, which are discussed for illustrative purposes only and do not limit the scope of the invention:

(1) As discussed with reference to FIG. 1D, in a first single-device, multi-player embodiment of the NEX system, a single mobile computing device may be used to capture a training video of multiple players in the same training area, where the multiple players may compete or cooperate in physically responding or reacting to a single visual cue augmented to the training video. The captured training video may first be analyzed to detect individual player images or player postures from one or more frames of the training video, and player image clusters or player posture flows may be established for individual players for tracking player motion during the training session. If players compete, the player who responds or reacts to the visual cue first may be awarded a positive point score while others are given a zero point score; if players cooperate, for example when training for a doubles game in tennis or badminton, point scores may be tallied across all players.

(2) In a second single-device, multi-player embodiment, a single mobile computing device may be used to capture a training video of multiple players in the same training area, where multiple, player-specific visual cues may be augmented to the same training video. That is, each player responds to his or her own visual cue. This embodiment is particularly useful when only a single large external display is available for facilitating training of multiple players, possibly at different skill levels.

(3) In a multi-device, multi-player embodiment of the NEX system for basketball dribbling training, two or more players or users of the NEX system may each dribble in front of a respective mobile computing device, each responding to randomly generated visual cues, at the same or different difficulty levels. Training scores may be exchanged periodically between the multiple devices in real time to keep players updated on other player's training performance. The training session may terminate when a first player reaches a target score.

(4) In another multi-device, multi-player embodiment, the same sequence of visual cues may be presented to all players, and augmented to all respective training videos captured by individual mobile computing devices. For a given visual cue, each player sees the same visual symbol at the same position in the image plane of his or her training video, although the exact time instance that such a visual cue appears within the training session may differ, based on how fast the player has been responding to individual visual cues. Again, training scores or other training data may be exchanged and compared periodically, or at the end of the training session. This sequence of visual cues may be viewed as a training challenge controlled the NEX system, enabling different players to train simultaneously, or at different, non-overlapping time periods asynchronously. The configuration of a sequence of visual cues may be based on a difficulty level of the training session.

(5) In a third multi-device, multi-player embodiment, the same sequence of visual cues again may be presented to all players and augmented to all respective training videos in real time, and players may compete in responding to the visual cue, for example touching a visual symbol, with the player who responds to the visual cue first awarded a positive point score, and other players awarded fewer or zero points based on their response quality. Response quality may be measured by a speed of the response, an accuracy measure for player movements, and/or other similar quality metrics. It would be understood by persons of ordinary skill in the art that such a real-time multi-player game has higher delay requirements to ensure synchronization among different players. In some embodiments, different players may be located at the same training area, with individual mobile computing devices connected via a local area network (LAN).

(6) Further expanding on the different multi-player embodiments above, players may be grouped into teams, where members of the same team may be located at the same training area, or at geographically different training areas. When a single training video is captured of multiple players in the same team, more than one visual cues may be augmented to the training video, to be responded by these players on the same team, in a coordinated or uncoordinated fashion, before a scored is tallied and a next set of visual cues is presented. In various embodiments, teams may compete on a total score, on a respective set of challenges, or on the same set of challenges in real-time.

Although NEX device 750 as shown in FIG. 7 serves as the core for a NEX platform 700, in some embodiments such as in multi-player training, NEX platform 700 may be networked among multiple user devices, where a NEX server implemented according to the embodiment shown in FIG. 3 may be connected to multiple camera-enabled user computing devices implemented according to the embodiment shown in FIG. 2, and each used to capture physical training data, and for providing player analytics. Such training video and/or analytics data may be uploaded to the NEX server, which in term may store and facilitate sharing of such data among individual players/users and teams.

Exemplary Convolutional Neural Networks (CNNs) for Pose Estimation

FIG. 8A is a block diagram 800 of an exemplary neural network for pose estimation, according to some embodiments of the present invention. Here neural network layers or blocks are drawn with thickened lines. In this illustrative example, a two-branch CNN efficiently detects poses of multiple people in an input image by predicting part confidence maps for body parts, and part affinity fields for body part-to-body part association, effectively decoupling the detection of a body part such as an arm or leg, and the assignment of the detected body part to an individual person. A part affinity field (PAF) is a 2D vector field that encodes the location and orientation of body parts including limbs over the image domain. A PAF encodes the association between body parts, where body parts belonging to the same person are linked.

The illustrative network shown in FIG. 8A performs the following steps to estimate the pose of one or more persons in an input image:

1. Use a convolutional network block as a feature extractor to compute a feature map from an input image;
2. Turn the feature map into a key point heat map and an affinity field heat map using another convolutional network block;
3. Refine the key point heat map and the affinity field heat map using yet another convolutional network block, and repeat for several times;
4. Use Rectified Linear Units (ReLU), separable convolutional layers and/or batch normalization techniques to improve the accuracy and performance of the network;
5. Compute final poses by linking the key points using the affinity field heat map.

More specifically, an input image 802 is first passed through a feature block 810 to generate a feature map 812. Initial prediction blocks 820 and 824 then extract a key point map 822 and an affinity field map 826, respectively. A concatenation operation 830 is performed before further refinements are carried out in multiple iterations. For each stage of iteration, refine blocks such as 832, 836, 842, and 846 predict refined key point maps such as 834 and 844, and refined affinity field maps such as 838 and 848, respectively. Concatenation operations such as 840 are performed to generate input for the next stage. A total of N refinements may be carried out, where N may be any positive integer. For example, N may equal to 5 in some embodiments of the present invention. After the last refinement stage, key point heat map 844 is examined in step 850 to find peaks as human joint points or key points 852. Such key points may be linked in step 860 to generate final poses 862, by performing bipartite matching using affinity field heat map 848 to compute weights between key points. In this illustrative example, key point map 844 may comprise 18 channels, while affinity field map 848 may comprise 34 channels.

FIG. 8B is a detailed block diagram illustrating an exemplary Feature Block 810, according to some embodiments of the present invention. In this example, separable convolutional layers (SCL) are deployed with different kernel and stride sizes.

Correspondingly, FIG. 8C is a detailed block diagram illustrating an exemplary separable convolutional neural network layer 870, according to some embodiments of the present invention. A depth-wise separable convolution or a separable convolution layer factorizes a conventional, full convolution operation into a first depth-wise convolution to filter the input channels, and a second point-wise convolution to combine outputs of the depth-wise network layer to build a feature map. Depth-wise separable convolutions trade significant improvements in computational efficiency for a small reduction in accuracy. Batch optimization and ReLU blocks further help improve the accuracy and performance of the network layer. Furthermore, in some embodiments, inverted residuals may be utilized to connect linear bottleneck layers between individual depth-wise separable convolutional layers, which also tradeoff computation and accuracy. Linear bottleneck layers reduce the dimensionality of the input, while inverted residuals use shortcut connections between the bottlenecks to enable faster training and better accuracy.

Figure 8D:
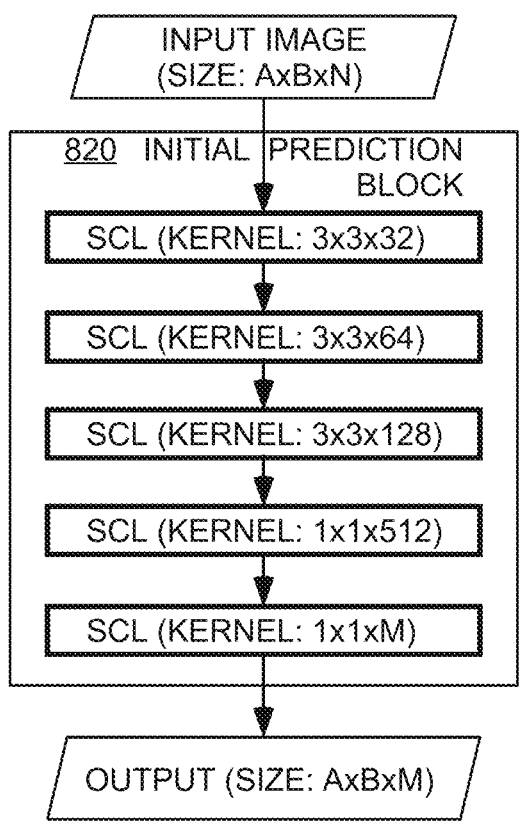
FIG. 8D is a detailed block diagram illustrating an exemplary Initial Prediction Block, according to exemplary embodiments of the present invention.
Figure 8E:
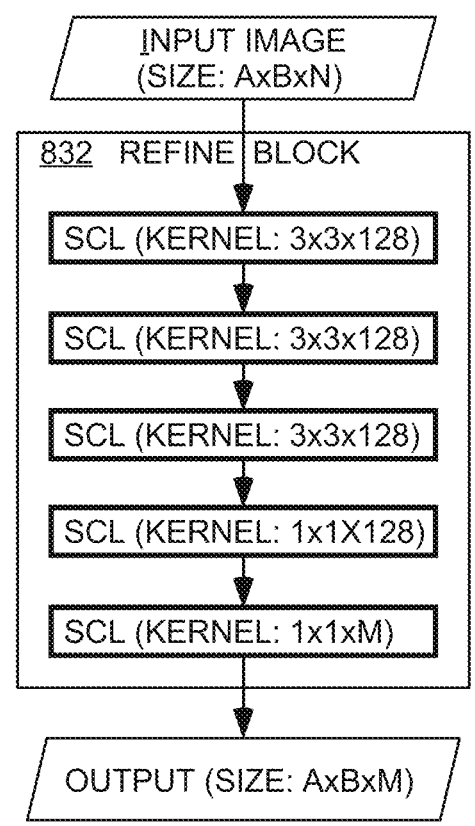
FIG. 8E is a detailed block diagram illustrating an exemplary Refine Block, according to exemplary embodiments of the present invention.

FIG. 8D is a detailed block diagram illustrating an exemplary Initial Prediction Block 820, according to some embodiments of the present invention; FIG. 8E is a detailed block diagram illustrating an exemplary Refine Block 832, according to some embodiments of the present invention. Both comprise multiple separable convolutional layers having different kernel sizes. The input, output, and kernel sizes shown in FIGS. 8A and 8E are for illustrative purposes only, and other similar hyperparameter values may be used in various embodiments of the present invention.

In some implementations of the present invention, one or more of existing software modules may be utilized, including but not limited to, CoreML for CNN object and key point detection, SceneKit for rendering an AR court, and CoreMotion for understanding a mobile device's orientation.

Exemplary Convolutional Neural Networks (CNNs) for Object Detection

Many sports and corresponding performance training methods or techniques require additional equipment, such as a ball, hoop, marker cones, hurdles, batons, rackets, and the like. The detection of moving and/or static non-human objects from the training video is needed for some training activities to help determine player actions and player analytics.

Figure 9A:
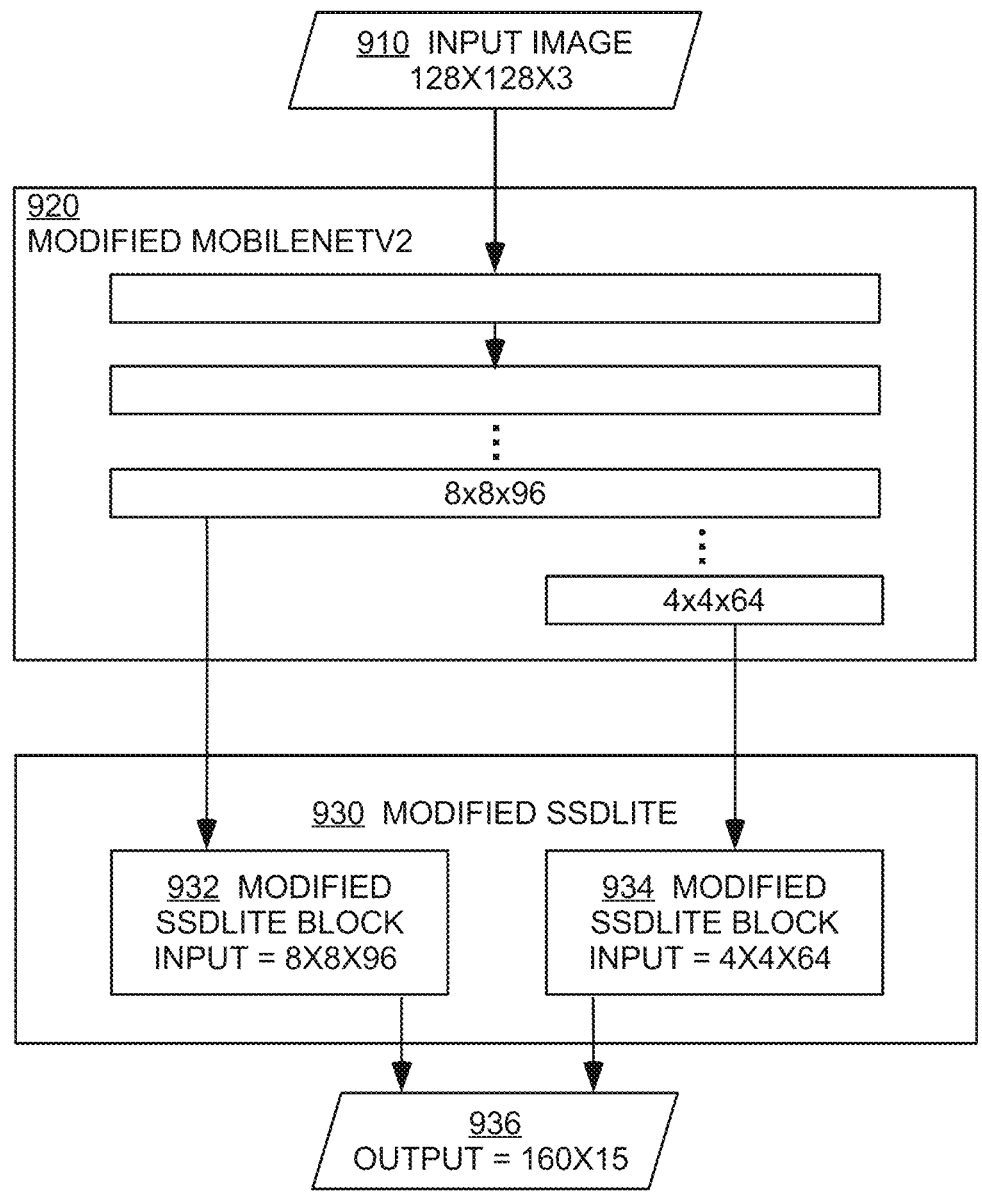
FIG. 9A is a block diagram of an exemplary neural network for ball detection, according to one embodiment of the present invention.
Figure 9B:
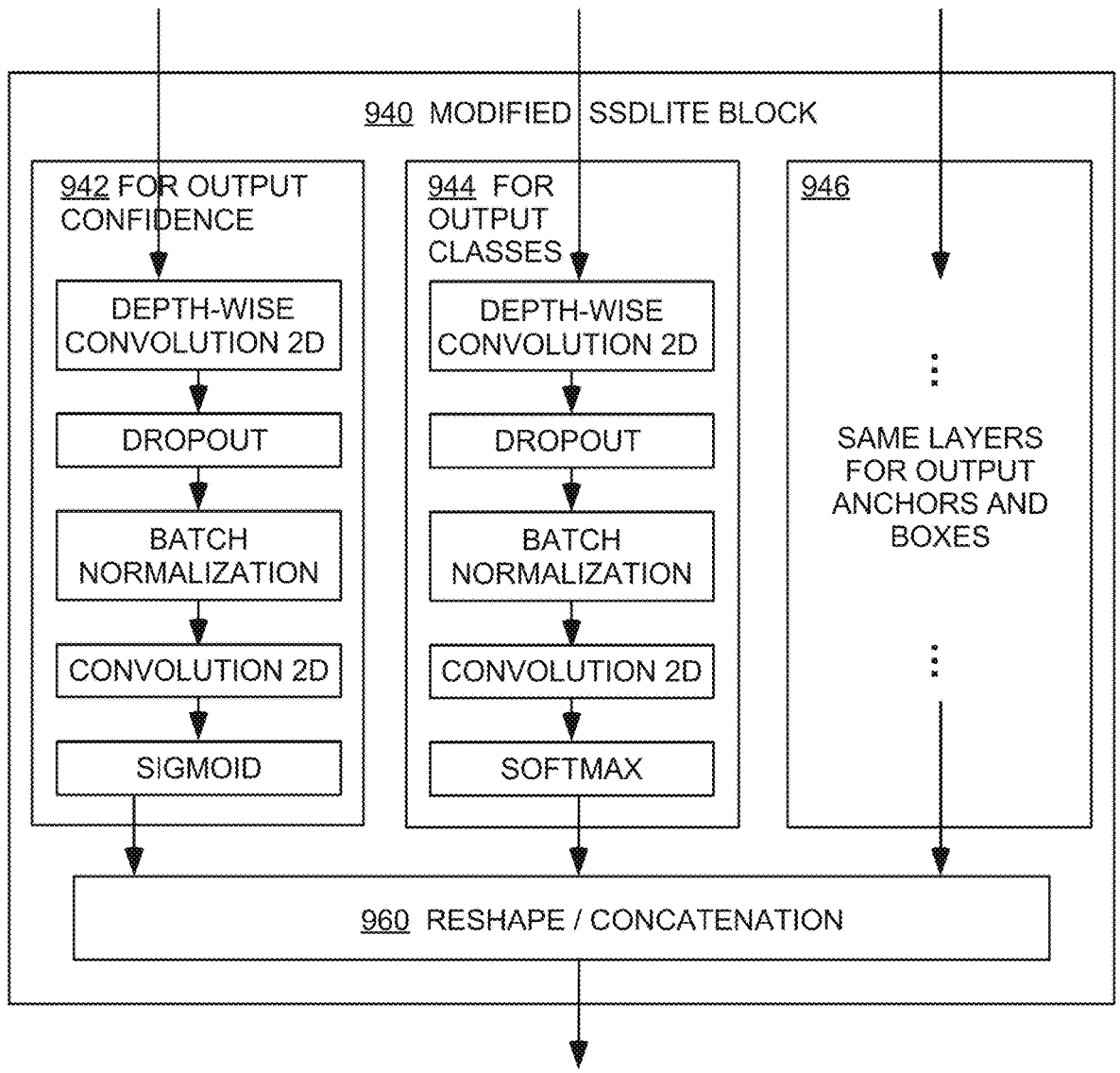
FIG. 9B is a detailed block diagram illustrating an exemplary Modified SSDLite Block, according to one embodiment of the present invention.

FIGS. 9A and 9B are respective block diagrams of an exemplary neural network for ball detection, according to one embodiment of the present invention. This object detector is presented for illustrative purposes only, and some embodiments of the present invention may utilize other computer vision system designs for object detection.

FIG. 9A is a block diagram 900 of an exemplary neural network for ball detection, according to some embodiments of the present invention. In particular, FIG. 9A shows a CNN-based ball detector utilizing an optimized, modified MobileNetV2 framework as a feature extractor and a modified SSDLite framework for multi-scale object detection. An input image 910 is first processed through a Modified MobileNetV2 block 920, the output of which is processed through a Modified SSDLite module 930 comprising two Modified SSDLite blocks 932 and 934, to generate output 936. The input, output, and kernel sizes shown in FIGS. 9A and 9B are for illustrative purposes only, and other similar hyperparameter values may be used in various embodiments of the present invention.

MobileNetV2 is an efficient convolutional neural network design for resource-constrained, mobile device-based computer vision applications. A first key building block of MobileNetV2 is depth-wise separable convolutions, which factorize a conventional, full convolutional operation into a first depth-wise convolution to filter the input channels, and a second point-wise convolution to combine outputs of the depth-wise network layer to build a feature map. Depth-wise separable convolutions trade significant improvements in computational efficiency for a small reduction in accuracy. A second key building block of MobileNetV2 is inverted residuals connecting linear bottleneck layers between individual depth-wise separable convolutional layers, which also tradeoff computation and accuracy. Linear bottleneck layers reduce the dimensionality of the input, while inverted residuals use shortcut connections between the bottlenecks to enable faster training and better accuracy.

Although not shown explicitly in FIG. 9A, in this exemplary embodiment, two MobileNetV2 output layers and 14 bottleneck operators may be used, a non-obvious reduction from the conventional setup with 6 MobileNetV2 output layers and 17 bottleneck operators. Such modifications optimize the feature extraction process to not only reduce the overall computational complexity but also improve the achievable accuracy by tailoring to the specific small input and ball detection goal.

FIG. 9B is a detailed block diagram illustrating an exemplary Modified SSDLite Block, such as 932 or 934 in FIG. 9A, according to some embodiments of the present invention. SSD refers to a Single Shot MultiBox Detector, a multi-object detection framework using a single deep neural network to discretize feature maps into multi-scale bounding boxes. SSD eliminates separate bounding box proposal generation and feature resampling stages to improve computation efficiency without compromising detection accuracy. SSDLite is a mobile-customized variant that utilizes depth-wise separable convolution in SSD prediction layers. Modified SSDLite block 940 shown in the exemplary embodiment of FIG. 9B further tailors and improves the accuracy of SSDLite by adding dropout layers.

More specifically, in Modified SSDLite Block 940, parallel network blocks 942, 944, and 946 are utilized to process the input data separately for output confidence, output classes, and output anchors and bounding boxes. Each block has the same architecture, comprising a depth-wise convolution in 2D space, dropout, batch normalization, further convolution, and a functional operation for classification. Feature maps thus generated are reshaped and/or concatenated via processing block 960 to generate output data.

For the ball detection task, two positive object classes may be considered: "ball" and "ball-in-hand." With conventional SSD or SSDLite framework, a single softmax function may be used to activate among background (e.g., no positive), and these two classes. By comparison, Modified SSDLite Block 940 is designed so that it may classify a ball out of a background, but does not always classify between ball and ball-in-hand for some training data. Such a design takes into account several factors. First, ball and ball-in-hand are not always distinguishable, even for a human. In addition to motion blur, background and other objects such as leg, arm, other people in the background could look like a hand in terms of shape and/or color. Second, having a classifier distinguish between ball and ball-in-hand may not always be worthwhile and may even compromise detection accuracy since there are "gray areas" where an input may be classified either way. Instead, within Modified SSDLite Block 940, a sigmoid function is used to produce confidence levels of whether a ball is present against a background, while a softmax function is used to classify between ball and ball-in-hand, or two output classes instead of three output classes for conventional SSD/SSDLite frames. As a further reduction to computational complexity, loss function and/or back propagation may be disabled if a given training case is in the "gray area."

Exemplary Statistics Generation for Virtual Coaching

Figure 10:
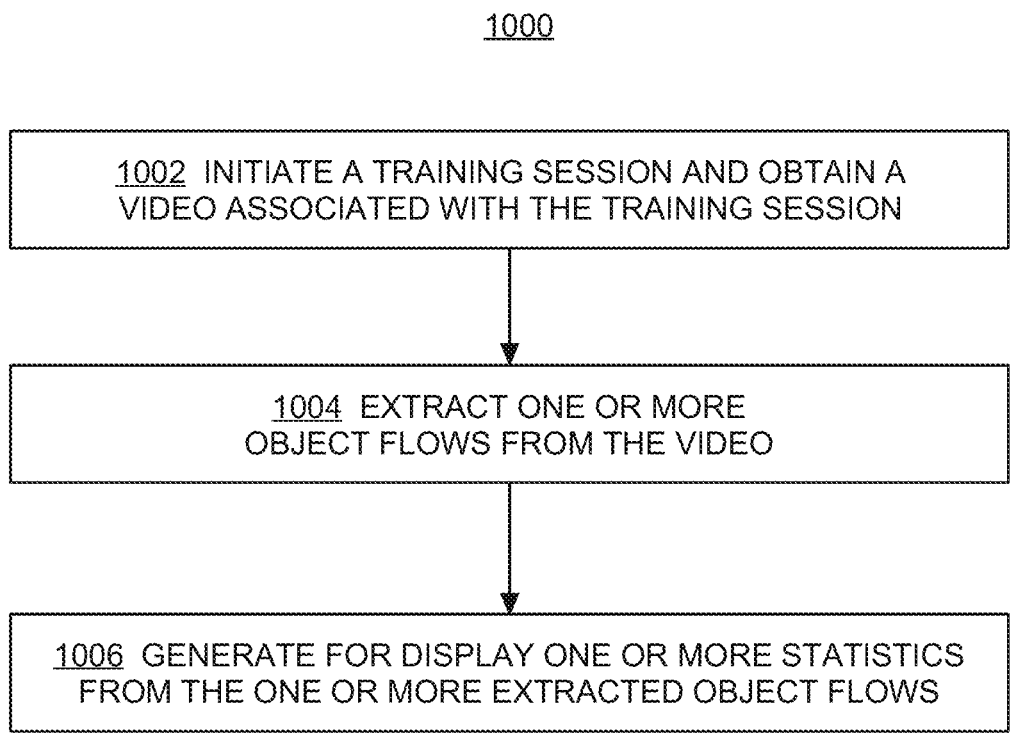
FIG. 10 shows a flowchart illustrating exemplary operations of a user device and associated algorithms for determining one or more statistics from a video of a training session, according to some embodiments of present invention.

FIG. 10 shows a flowchart 1000 illustrating exemplary operations of a user device and associated algorithms for determining one or more statistics from a video of a training session, according to some embodiments of present invention. At step 1002, a training session may be initiated, and a video associated with the training session may be obtained. At step 1004, one or more object flows are extracted from the video. At step 1006, the one or more extracted object flows may be used to generate one or more statistics, which may be displayed on the user device, on a networked external display, or stored in memory for later use. While not shown in FIG. 10, additional steps such as device calibration may occur before step 1002. Similarly, additional steps may occur in between steps 1002 and 1004, and in between steps 1004 and 1006, such as various AI-based machine vision algorithms, such as but not limited to convolutional neural networks (CNN), and the like, as described above. Finally, while not shown in FIG. 10, additional steps may occur after step 1006, such as storing the statistics, transmitting the statistics to a server, and the like.

Virtual Coaching and Training of Basketball Dribbling for Body-Eye Coordination

Example operations described herein and in particular, the example operations described above in connection with FIGS. 1 to 10 may be performed by an application running on an electronic device, such as shown and described in connection with FIG. 2 above.

Figure 11:
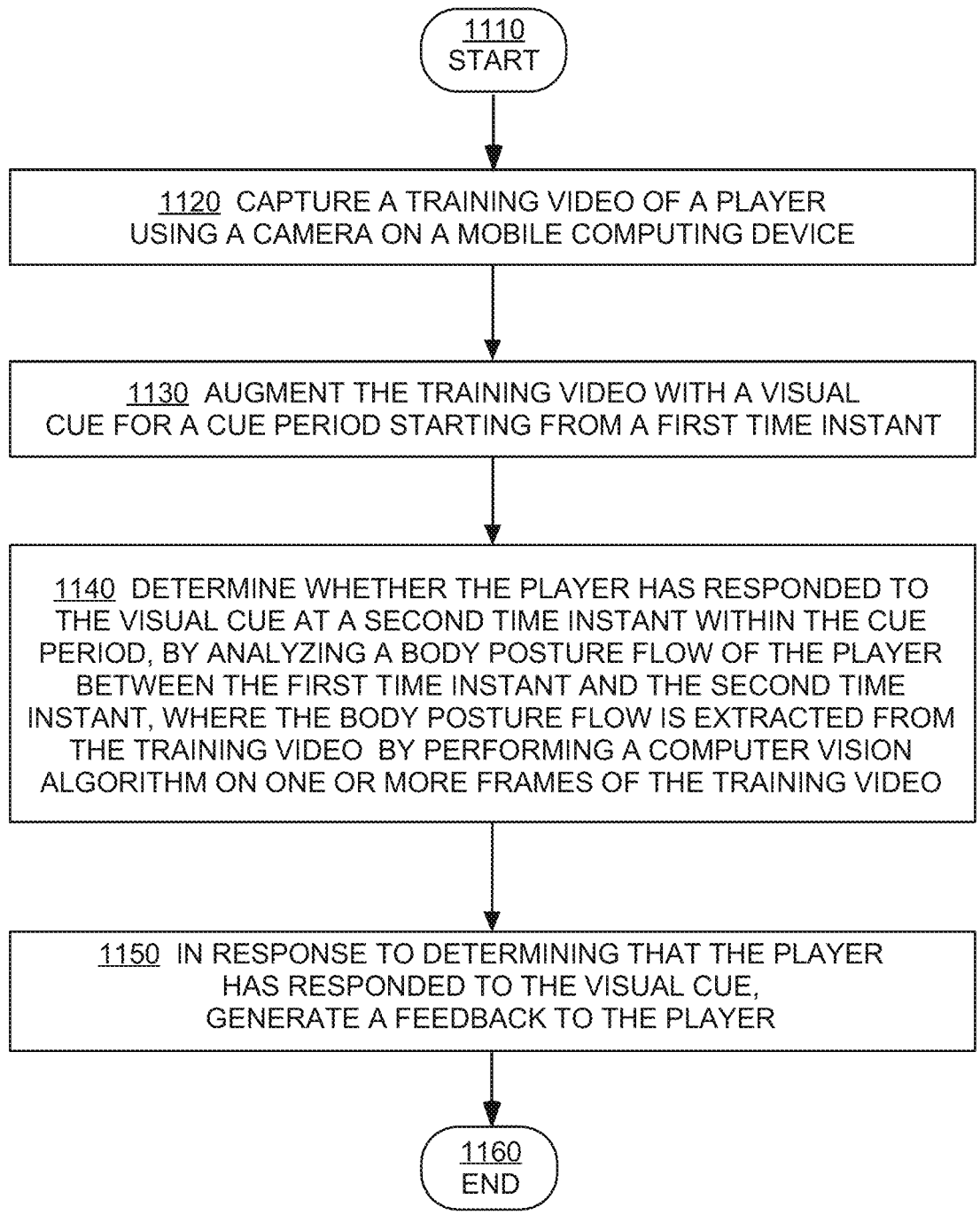
FIG. 11 shows a flowchart illustrating exemplary operations for interactive virtual coaching and training, according to some embodiments of the present invention.

FIG. 11 shows a flowchart 1100 illustrating exemplary operations for interactive virtual coaching and training, according to some embodiments of the present invention. Upon initiation at step 1110, a training video is captured at step 1120 of a player, using a camera on a mobile computing device. At step 1130, the training video is augmented with a visual cue for a cue period starting from a first time instance. At step 1140, a body posture flow of the player is analyzed to determine whether the player has responded to the visual cue at a second time instant within the cue period, where the body posture flow is extracted from the training video by performing a computer vision algorithm on one or more frames of the training video. In step 1150, a feedback is generated in response to determining that the player has responded to the visual cue.

Training Initiation and Device Calibration

Figure 12A:
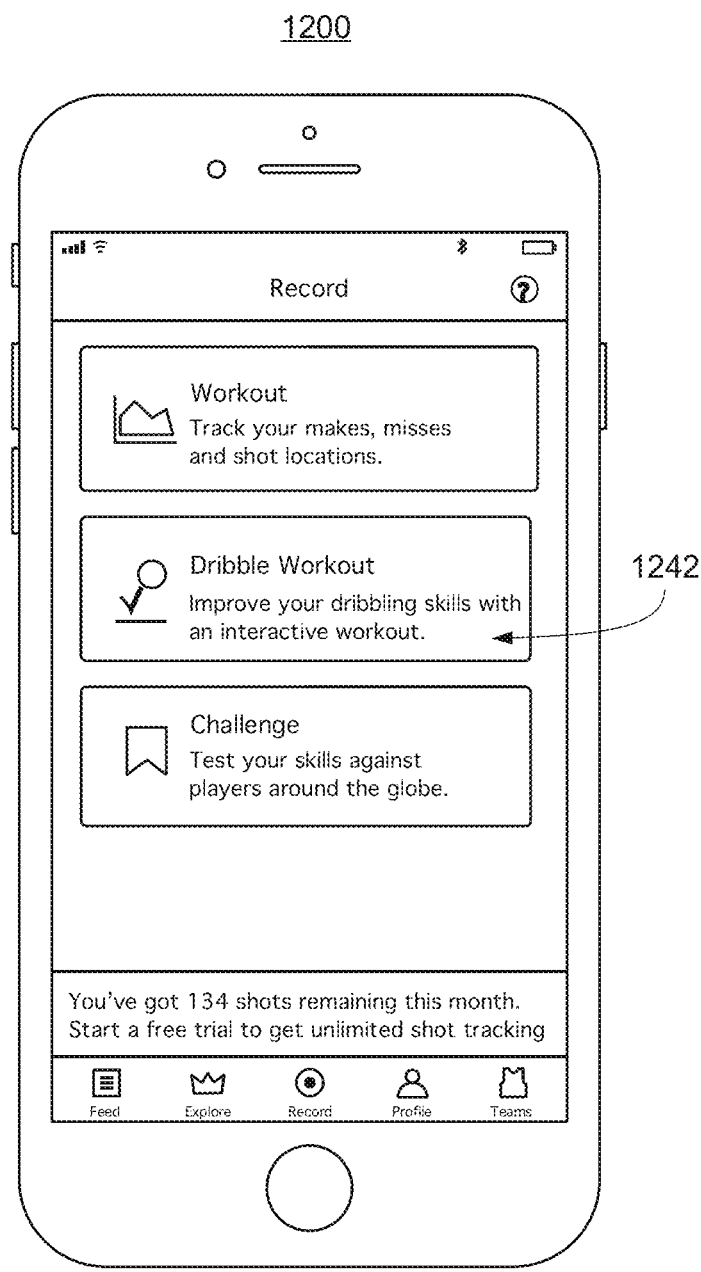
FIG. 12A shows a diagram representing an exemplary application running on a mobile computing device, in which an exemplary dribbling workout may be selected, according to some embodiments of the present invention.
Figure 12B:
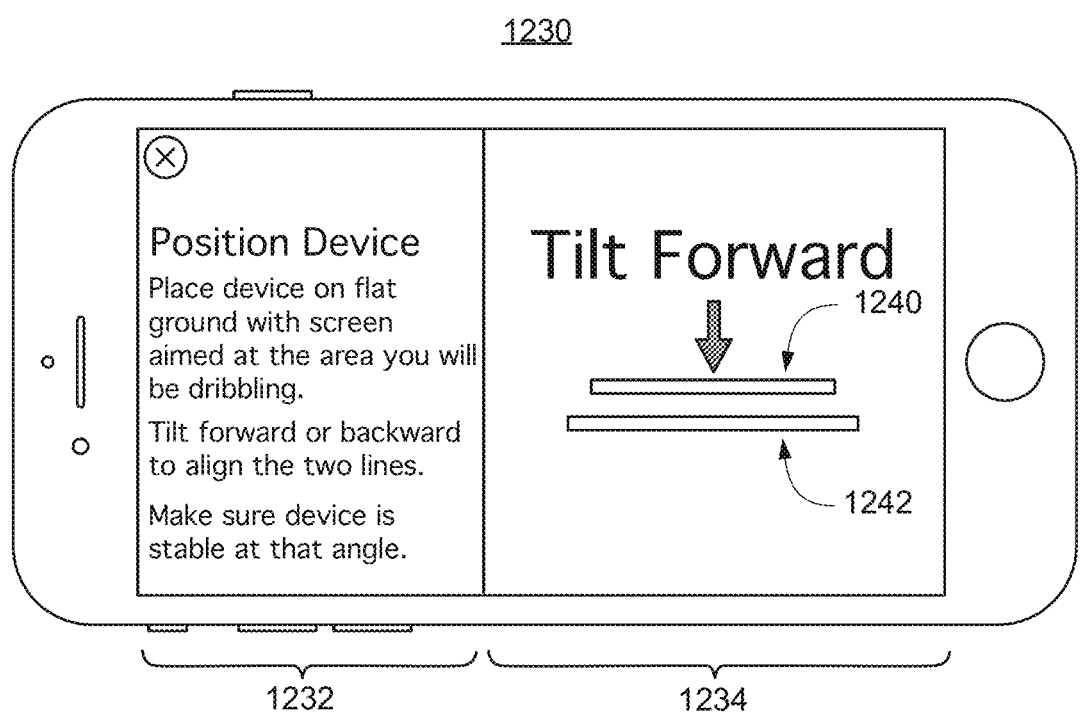
FIG. 12B shows a diagram representing an exemplary application running on a mobile computing device, in which the mobile computing device may be oriented and calibrated for interactive virtual coaching, according to some embodiments of the present invention.

To initiate a training session, the mobile computing device may first be adjusted for levelness, distance from the player, brightness under a current lighting condition, and other similar environmental parameters. FIG. 12A shows an exemplary diagram 1200 representing an exemplary application running on the mobile computing device, in which an exemplary dribbling workout may be selected, according to some embodiments of the present invention. FIG. 12B shows a diagram 1230 of an interface for optionally orienting and calibrating the mobile computing device for interactive virtual coaching, according to some embodiments of the present invention.

In FIG. 12A, the user may select a first option such as "Dribble Workout" 1242 in order to open the setup screen 1230 for device calibration. Other single or multi-player workouts and challenges may be selected via similar interfaces.

In FIG. 12B, the mobile computing device is orientated in the landscape direction. Instructions 1232 are displayed to the user to place the device on flat ground, with a front facing camera aimed at the area where the player will train, and with the display screen facing the player. When placed on the ground, the device may be tilted to achieve a certain inclination at which the training actions can be captured entirely. On the right side, graphical symbols are shown to assist the player in tilting the device to a desired 18 degrees. A symbol such as a top line 1240 may be configured to move in a correlated manner as the angle of the mobile computing device changes when the user tilts the device forward or backward, with respect to a baseline vertical orientation. The user may be able to match top line 1240 with a reference line 1242 that may correlate to approximately 18 degrees from a perpendicular posterior tilt. In one embodiment, a "Tilt Forward" instruction and/or a "Tilt Backward" instruction may be presented to the user depending on which direction from 18 degrees the device is oriented with respect to the reference vertical orientation. In some embodiments, when the user device maintains a given predetermined angle for a predetermined period of time, for example, approximately 3 seconds, the next user interface may be configured to automatically appear on the display of the user device. In some embodiments, the device orientation and calibration process shown in FIG. 12B is optional and may be skipped. For example, the user may choose to place the mobile computing device on a tripod above ground level at an appropriate height such that the tiling process is skipped entirely. In some embodiments, depending on the nature of the training activity, the player may be required to place the mobile computing device in a portrait orientation. In some embodiments, a given symbol such as an "X" may serve to abort the workout session on the user device to bring the user back to a home screen.

Figure 12C:
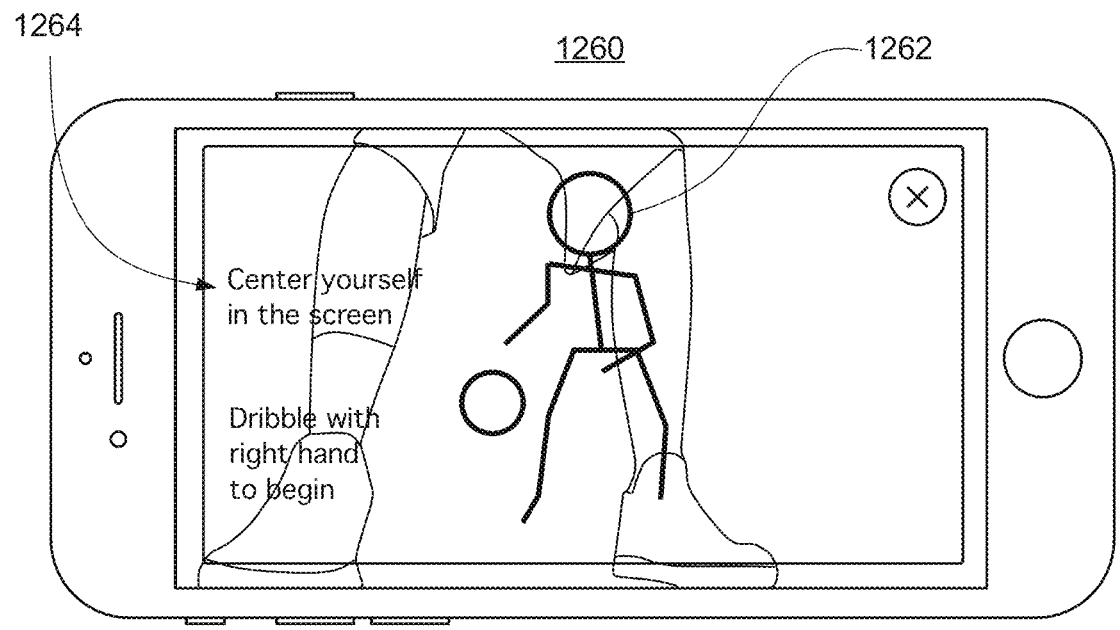
FIGS. 12C and 12D show respective diagrams representing an exemplary application running on a mobile computing device, in which an interactive workout session may be started with posture control, according to some embodiments of the present invention.
Figure 12D:
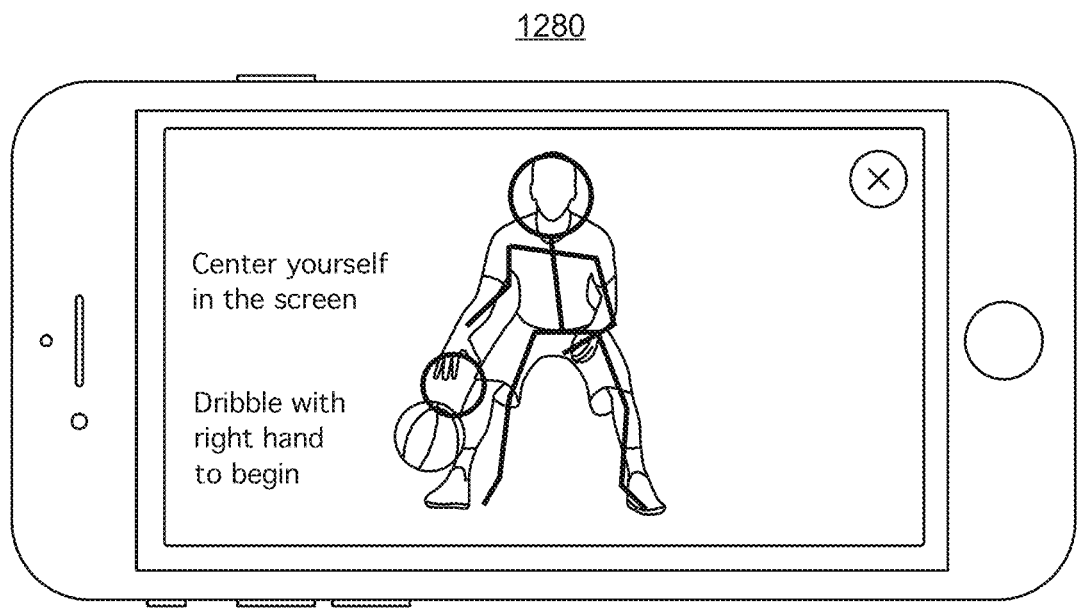
Figure 13A:
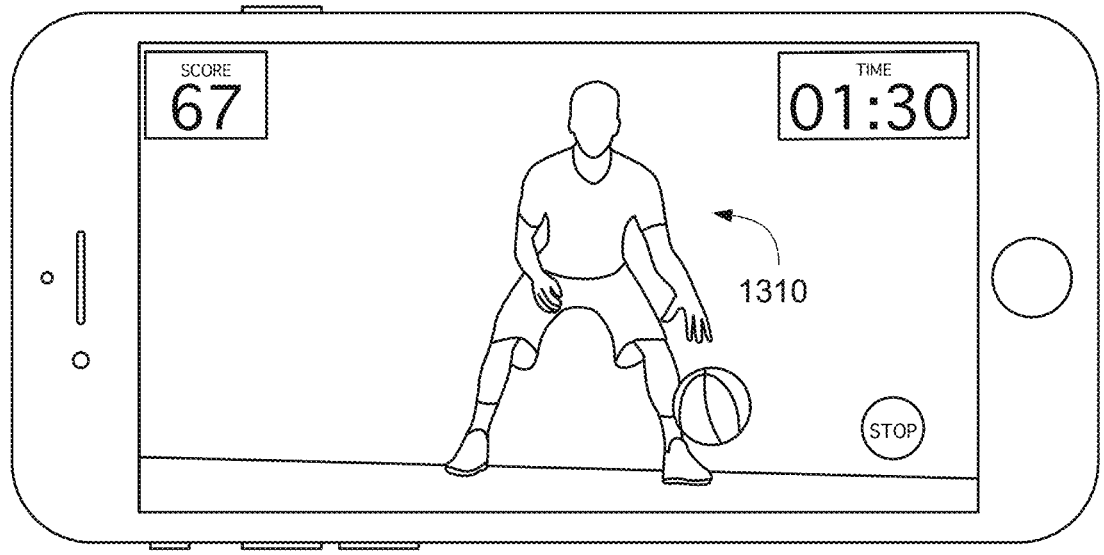
FIGS. 13A, 13B, 13C, and 13D show respective diagrams representing an exemplary virtual coaching and training application running on a mobile computing device, which facilitates an interactive dribbling session, according to some embodiments of the present invention.
Figure 13B:
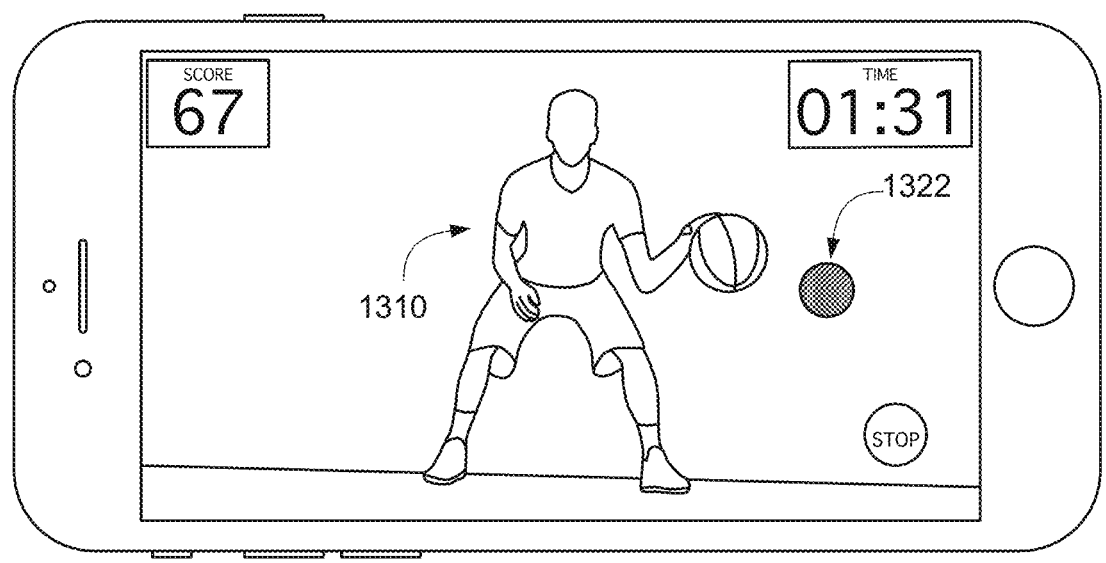
Figure 13C:
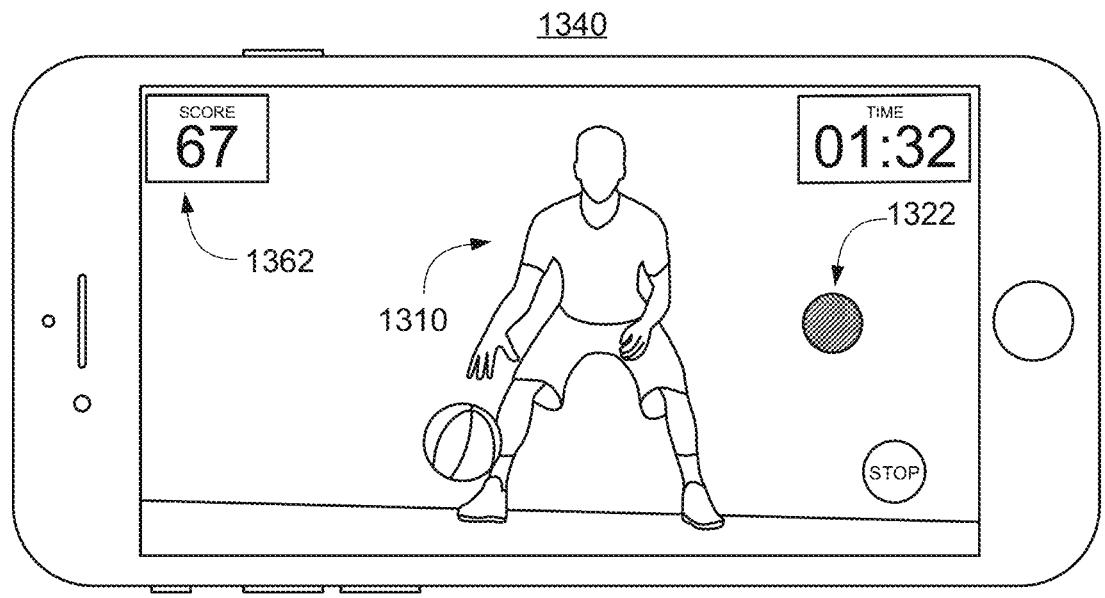
Figure 13D:
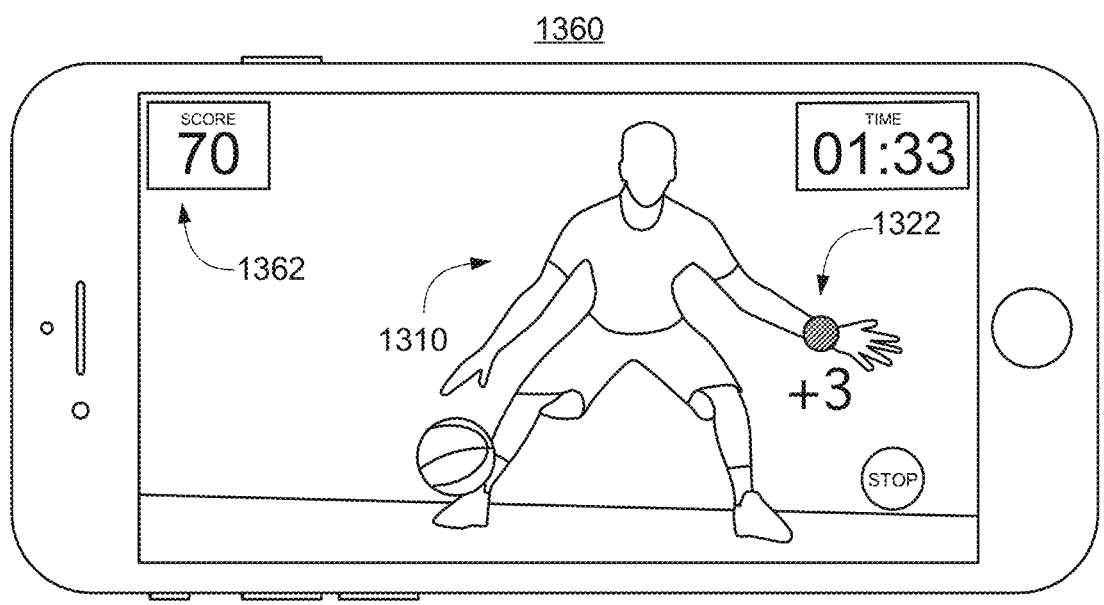

FIGS. 12C and 12D show respective diagrams 1260 and 1280 of an interface for starting an interactive workout session with posture control, according to some embodiments of the present invention. In this exemplary embodiment, the user may first position himself at an appropriate distance from the user device in accordance with one or more instructions 1264 presented to the user on a display screen of the user device. A wireframe figure 1262 may be presented to provide a reference scale for the user, with the user backing away from the mobile computing device until his image approximately overlaps with wireframe figure 1262, as shown in FIG. 12D. For other basketball training activities or other sports, the user may be required to move closer to or farther away from the mobile computing device, and the desired scale may be achieved by adjusting the size of wireframe figure 1262. Once the user performs a predetermined activity such as a given number of uninterrupted dribbles, the workout session may automatically start.

In various embodiments, instructions 1264 may vary based at least in part on the nature of the training activity, the nature of environment in which the training is being performed, such as dimension of a room in which the training session is being performed and the like, combinations thereof, and/or the like. In this embodiment, once the user performs a predetermined activity, such as a given number of uninterrupted dribbles, the workout session automatically starts. There may be many other ways to start a workout session, including, but not limited to, providing a verbal cue to the user device, setting a timer to automatically start the workout, having another user provide input to the user device to start the workout session, using a separate device such as a smart watch signal to start the workout session, combinations thereof, and/or the like. Again, a given symbol such as an "X" or a "stop" icon may serve to abort the workout session on the user device to bring the user back to a home screen.

Interactive Training

FIGS. 13A, 13B, 13C, and 13D show respective diagrams 1300, 1320, 1340, and 1360 of an interactive dribbling session facilitated by an exemplary interactive virtual coaching and performance training application running on a mobile computing device, according to some embodiments of the present invention. More specifically, screenshots of a training video are shown as a training session is underway. In this example, presentation of the NEX application running on the user device, and interaction by the user with the virtual setup presented by the NEX application may serve to help the user improve hand-eye coordination and the user's reaction times.

Generally, for a chosen training activity, a given workout session, or a portion of the given workout session, may have a predetermined total training duration, such as 3 minutes or 30 minutes. A training session may also last until a user request is received to terminate. Once the training session is being recorded by a camera on the mobile computing device, after a wait time, a visual cue may be augmented onto the training video. For example, the visual cue may appear at a pre-determined location or a random location on the image plane of the training video.

A duration of the wait time for the visual cue may be fixed or random, and may be user-configured, or automatically configured by the NEX application, optionally based on a difficulty setting of the training session. A wait time may be measured from the beginning of the training session first, then from the end of a last set of player movements. In this dribbling example, a randomly determined wait time after which the visual cue appears may be a time associated with a randomly generated number of dribbles that the user performs, such as between 4 to 10 dribbles. From diagram 1300 to 1320, approximately one second has lapsed before a visual cue 1322 appears on the screen, towards user 1310's left side.

Once augmented onto the training video, the visual cue may last a fixed or a random cue period. A duration of this cue period may be predetermined, user-configured, automatically configured by the NEX application, optionally based on a difficulty setting of the training session, or based on a user response to the visual cue.

In different embodiments, the visual cue may be a textual message or a graphical symbol, indicative of an instruction, prompt, or stimulus to evoke a physical response from the user, in the form of a body movement or a sequence of body movements. In the example shown in FIGS. 13A to 13D, visual cue 1322 is a large dot indicative of a target for user 1310 to touch virtually with a non-dribbling hand. Visual cue 1322 is superimposed onto the training video, at a position located to the left of user 1310 when user 1310 is dribbling with his left hand in diagram 1320. To respond to this visual cue, user 1310 passes the ball from his left hand to his right hand first in diagram 1340, then extends his non-dribbling hand towards the left to touch displayed symbol 1322 in diagram 1360. After user 1310's left hand remains in the frame of the target symbol 1322 for a predetermined period of time, such as approximately 0.4 seconds, the symbol may disappear from the training video, as presented to the user in this example. The disappearance or removal of the cue symbol may occur immediately, or gradually by shrinking the symbol in size or fading the symbol in color. The cue period may be defined as the time period during which the visual cue is augmented to, or virtually present in the training video. The disappearance of the visual cue symbol may be viewed as a feedback to the user, such that the user may retract the extended non-dribbling arm and continue the dribble activity with either hand. The NEX system may then restart the process of waiting for a randomly determined number of dribbles by the user before a new visual cue symbol is augmented onto the training video as a virtual target.

In addition to being a shaded or colored dot, the visual cue may alternatively be one or more other symbols such as a horizontal virtual line above the user's head for the user to touch with his head by jumping up, two vertical virtual lines for the user to touch with respective hands or feet when running laterally from side-to-side, a distant virtual goal for the user to shoot a ball towards, a set of virtual cones for the user to move around or dribble around in a predetermined pattern, or a set of virtual markers for the user to jump step in a specific pattern or order. Similarly, in some embodiments, the visual cue may indicate an area that the user can move towards, into, or out of; in some embodiments, the visual cue may indicate one or a sequence of directions towards which the user can move a body part towards, for example, rotating his head left or right, or lifting his chin up. Again, the visual cue may be any textual message or a graphical symbol, indicative of an instruction, prompt, or stimulus to evoke a physical response from the user, in the form of a body movement or a sequence of body movements.

As described with reference to FIGS. 13A to 13D, the physical response from the user may comprise a body movement to virtually touch a target visual cue with a body part such as hand, head, nose, forehead, finger, wrist, arm, elbow, leg, knee, foot, ankle, hip, and the like, in the image plane. The user may extend, bend, squat, lunge, push, pull, jump, leap, spin, rotate, balance, run, shoot, swing, bat, or perform other similar actions as instructed by the NEX application to complete the physical response. In some embodiments, the physical response may comprise a player movement to virtually touch the visual cue with a sports equipment object such as a ball, a rope, a baton, a racquet, and the like, again in the image plane. In some embodiments, the physical response may comprise a particular body movement or sequence of body movements, such as one or more back squats, split squats, pull-up, pushup, lateral plyometric jumps, forward high knee running, lateral side-to-side running, jumping jacks, shuttle runs, and the like. A quality of the player body movements may be determined by the NEX application via one or more computer vision algorithms, and a physical response may be deemed completed only if the quality of the player body movement is satisfactory.

To determine that the player has responded to the visual cue, one or more frames of the training video are analyzed using one or more computer vision algorithms. For example, as discussed with reference to FIG. 1D, and FIGS. 8A to 9B, one or more CNNs may be applied to some or all frames of the training video as the video is being captured to detect objects such as basketballs or soccer balls, and individual user and their postures. Input video frames may be downsampled in spatial or temporal domain to reduce the needed computation complexity. A tracking algorithm may be performed to track all detected objects and postures, to generate one or more object flows including one or more user posture flows. By examining the motion sequence and/or location of key feature points of a posture flow, such as those for a hand and fingers, the NEX system may determine whether and when the user has responded to the visual cue. Each CNN may be implemented in a separate software or hardware module on the mobile computing device, and each CNN may have been trained using one or more prior training videos.

In some embodiments, a quality point score may be earned by the user based on a characteristic of the user's physical response, such as accuracy or duration. For example, the visual cue symbol may be displayed for a predetermined amount of time, such as approximately 5 seconds, which may be configurable by the user and may be based at least in part on a difficulty setting associated with the training session. After 5 seconds, the visual cue symbol may disappear from the view presented at the display of the user device, if the user has not responded successfully by virtually touching the visual cue. The point score associated with accurately virtually touching the cue symbol by the user's non-dribbling hand may be configured to decrease in value over time. For example, the point score may start at 10 points for a reaction time of less than 0.5 seconds, and decrease at the rate of about 1 point every approximately 0.5 seconds, leading to a score range between 0 and 10. A reaction time may be computed as the time between when the visual cue first appears, and the time instant when the physical response is detected by the computer vision algorithms. A section of the view presented to the user, such as virtual scoreboard 1362 shown in FIGS. 13C and 13D, may be updated accordingly. In this disclosure, a reaction time is considered synonymous to a reaction speed.

In various aspects, such a training session design may serve to allow for users having a wide range of performance capabilities to benefit from a training session. For example, in the described basketball training session, dribbling faster may make cue targets appear quicker; accordingly, the virtual training session may serve to directly correlate a dribble frequency required by the user to a difficulty level of the training session. Moreover, in some embodiments, the higher the difficulty of the training session, or the more stringent the performance criteria for successfully completing a training session may be, the higher the final score may be awarded to a given user.

Once it is determined that the player has responded to the visual cue, a feedback may be generated to the player. In various embodiments, such a feedback may take on different forms and/or serve different purposes. For example, the disappearance or removal of the visual cue from the training video may be considered as a feedback to the user to signal that a current round or instant of the training has completed, and the player may restore to a startup posture; the point score as discussed above may also be considered a feedback, indicative of how fast the user has successfully responded to the visual cue. In some embodiments, the feedback may be a congratulatory audio message generated based on a current point score, a cumulative point score, or characteristics of the physical response elicited from the user. In some embodiments, the feedback may be a review of the user's form in responding to the visual cue, and instructions on how to achieve a better form. This feedback to the player may or may not be communicated to the player in real-time, in the form of a visual or audio display to the user.

Training Performance Review

Figure 14:
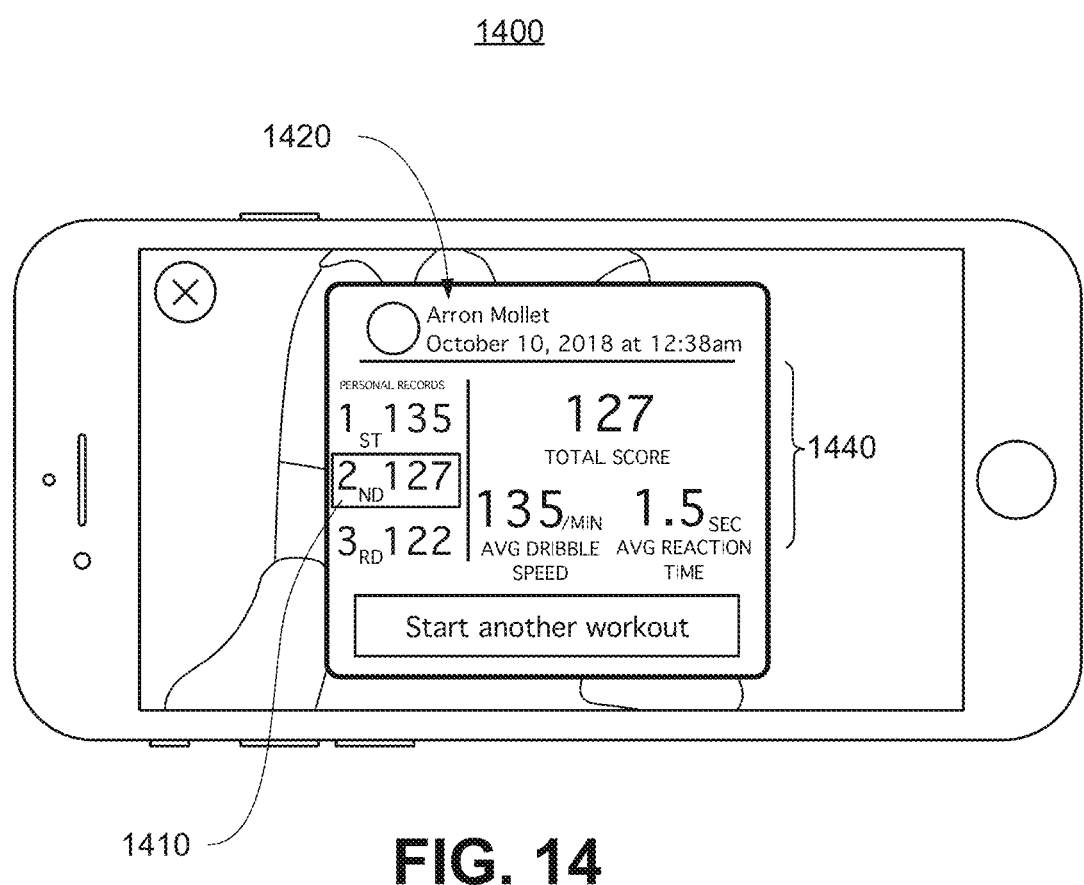
FIG. 14 is a diagram representing an exemplary interactive virtual coaching and training application running on a mobile computing device, in which user statistics are collected from an interactive dribbling session facilitated by the application, according to some embodiments of the present invention.

FIG. 14 is an exemplary diagram 1400 of user statistics and scores collected from an interactive dribbling session facilitated by an exemplary interactive virtual coaching and training application running on a mobile computing device, according to some embodiments of the present invention. In various embodiments, when a training session either expires or is aborted or terminated, for example, via a user input indicative of an abort operation, a review screen such as 1400 may be displayed to the user at the user device. The review screen may display various metrics 1440 associated with the performance of the user 1420 in the particular training session, including, but not limited to, the user's final obtained score, and a ranking 1410 of the current score as compared to the user's personal historical records. Moreover, the user may be presented with the option of starting another workout as part of the review screen or as part of another screen. In some embodiments, the user may be served with the option to begin another workout from the displayed review screen so that the user may leave his user device in place and thereby avoid the need to go through a device setup or calibration for consecutive workouts. Again, a given symbol such as an "X" may serve to abort the workout session on the user device to bring the user back to a home screen.

Figure 15A:
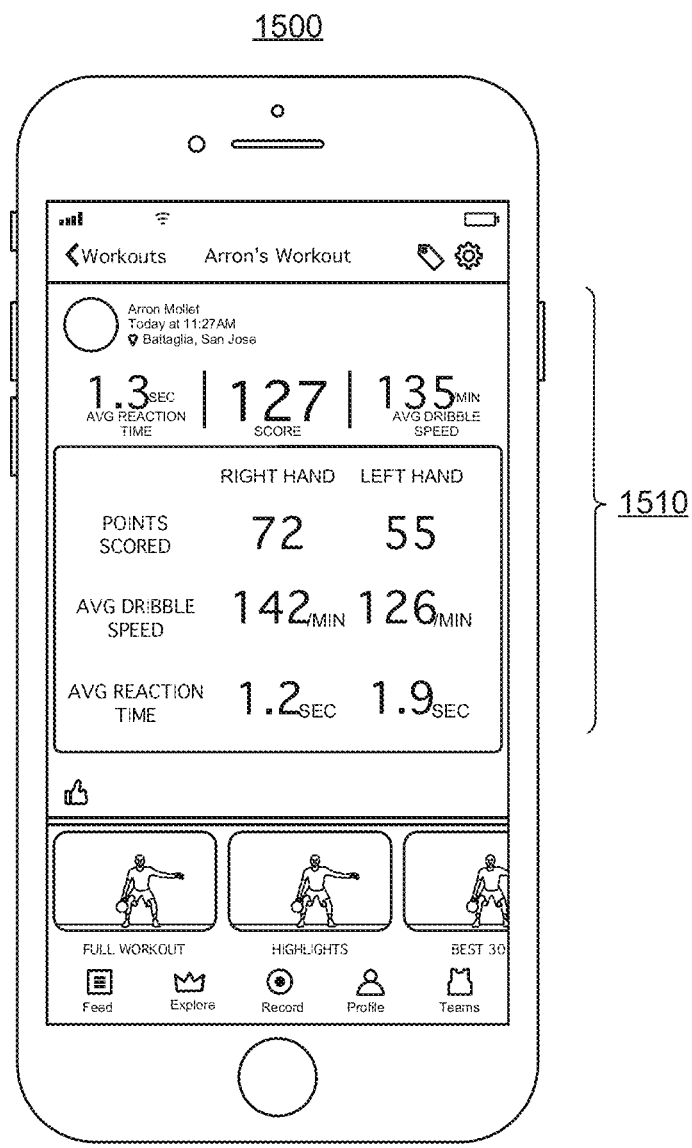
FIGS. 15A and 15B show respective diagrams representing an exemplary virtual coaching and training application running on a mobile computing device, in which player statistics and global rankings are displayed for interactive dribbling sessions facilitated by the application, according to some embodiments of the present invention.
Figure 15B:
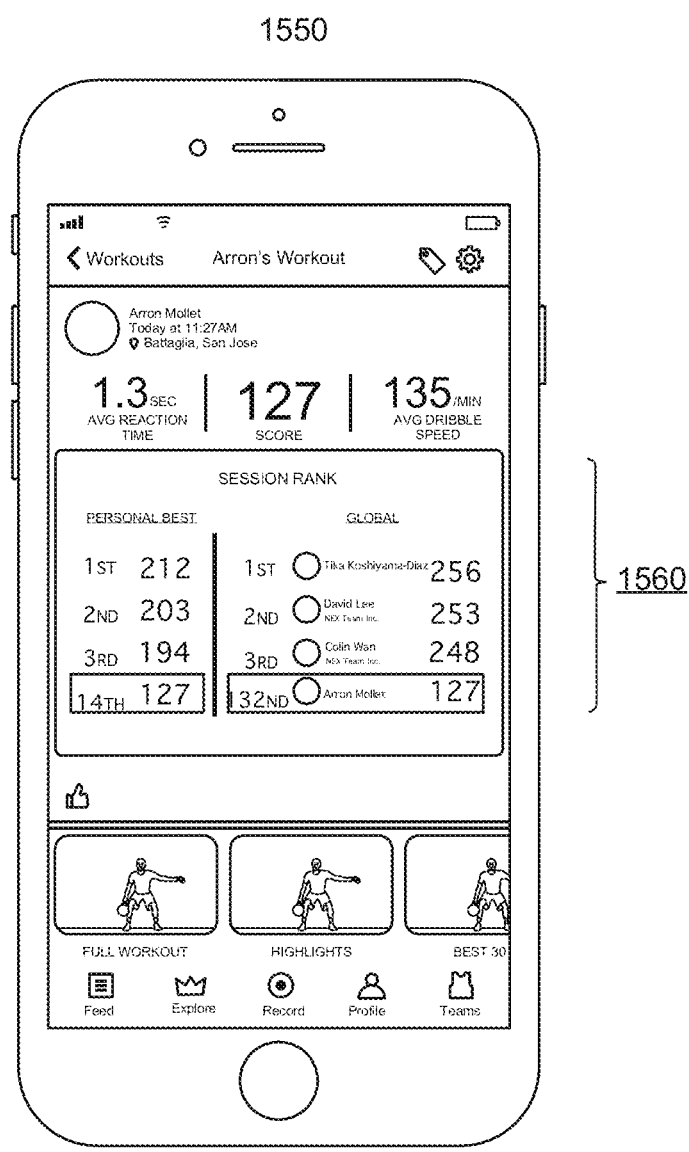

FIGS. 15A and 15B show respective diagrams 1500 and 1550 of player statistics 1510 and global rankings 1560 for interactive dribbling sessions facilitated by an exemplary interactive virtual coaching and training application running on a mobile computing device, according to some embodiments of the present invention. The NEX application allows for the presentation of a workout review to the users at the display of the user device. In one embodiment, such a workout review may allow the user to select, for example via a swiping motion at the user device having a touch screen, between statistics related to their performance for a given workout session, and a comparison of the given workout session statistics to the user's own previous workout sessions in addition to other user's best workout session statistics. In one embodiment, the application may be configured to display a video option to the user at the user device. In particular, the selection of the video which may be positioned anywhere on the display of the user device, such as in the lower section of the display of the user device, may provide the user with the option to view a portion or the entirety of the workout session. In some embodiments, the selection of the video option may be configured to process the video of the workout session (e.g., using one or more AI-based algorithms) to show key features (e.g., highlights) of a predetermined duration (e.g., a 30 sec highlight compilation) associated with the performance of the user during the workout session. For example, such a presentation may be configured to show the quickest reactions, or the continuous 30 sec segment in which the most points were scored by the user in performing a given workout and/or training activity. Moreover, the determination and presentation of such statistical reviews to the user may serve to provide insight into areas of user deficiency and strength with respect to one or more portions of the workout session such that users may easily identify where the most improvement is needed. As noted, various AI-based algorithms (e.g., neural networks, convolutional neural networks, Bayesian techniques, random forests, combinations thereof, and/or the like) may be used to automatically analyze and identify the areas of user strength and deficiency without explicit user identification.

Figure 16:
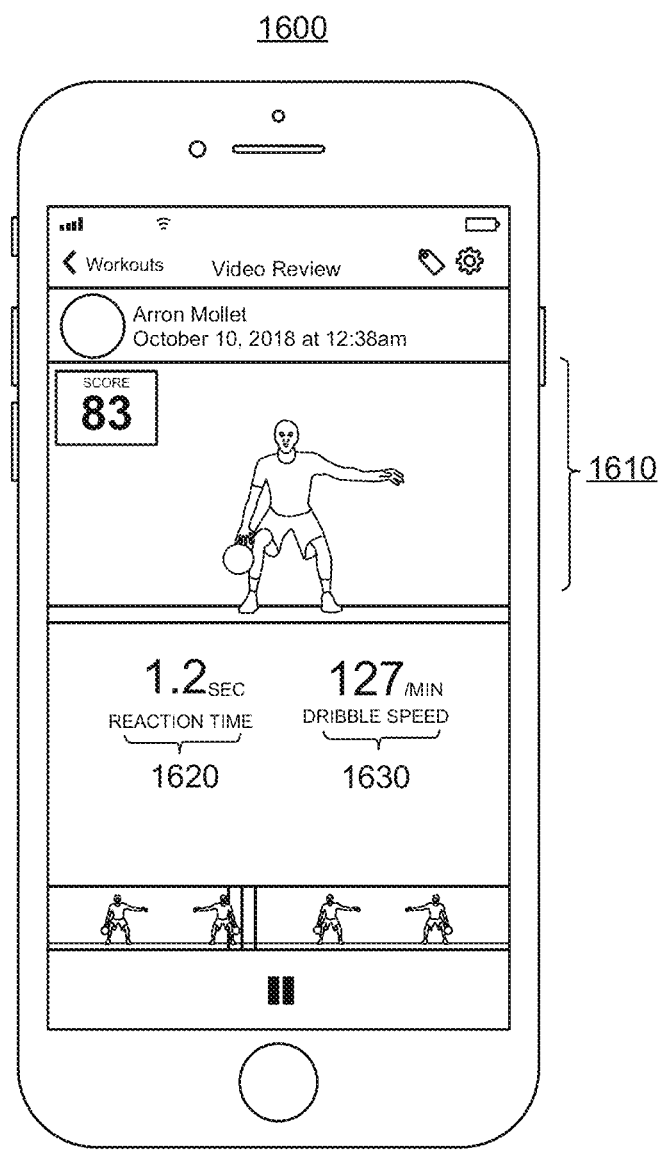
FIG. 16 shows a diagram representing an exemplary interactive virtual coaching and training application running on a mobile computing device, in which a video review of highlights of the user's performance may be provided in a feed, according to some embodiments of the present invention.

FIG. 16 shows a diagram 1600 of a video review 1610 of highlights of the user's performance, according to some embodiments of the present invention. As noted, a video review may display various statistics related to the user's performance during the training session. For example, the video review may serve to describe and display the reaction time 1620 of each individual reaction of the user as the video presentation progresses in time. In another embodiment, in the case of a basketball training session, a metric such as the dribble speed 1630 of the user may also be a live metric allowing the user to analyze their dribble speed and effort while performing the activities associated with the training session.

Figure 17:
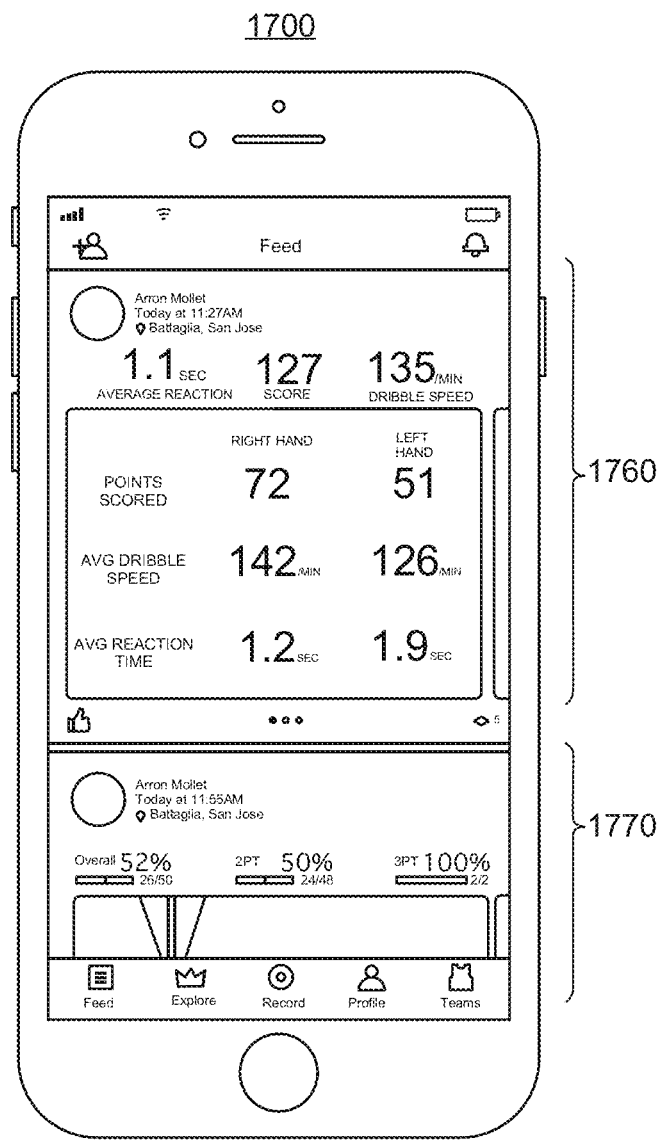
FIG. 17 shows a diagram representing an exemplary interactive virtual coaching and training application running on a mobile computing device, in which player statistics are provided in a feed, according to some embodiments of the present invention.

FIG. 17 shows an additional diagram 1700 of player statistics provided in a feed, according to some embodiments of the present invention. In one embodiment, such a feed may be in the form of a feed card 1770 that may feature a highlight video (e.g., an approximately 30 second highlight) of a given workout and a statistical review 1760 of the performance of the user during the given training session.

Other Exemplary Embodiments

Figure 18:
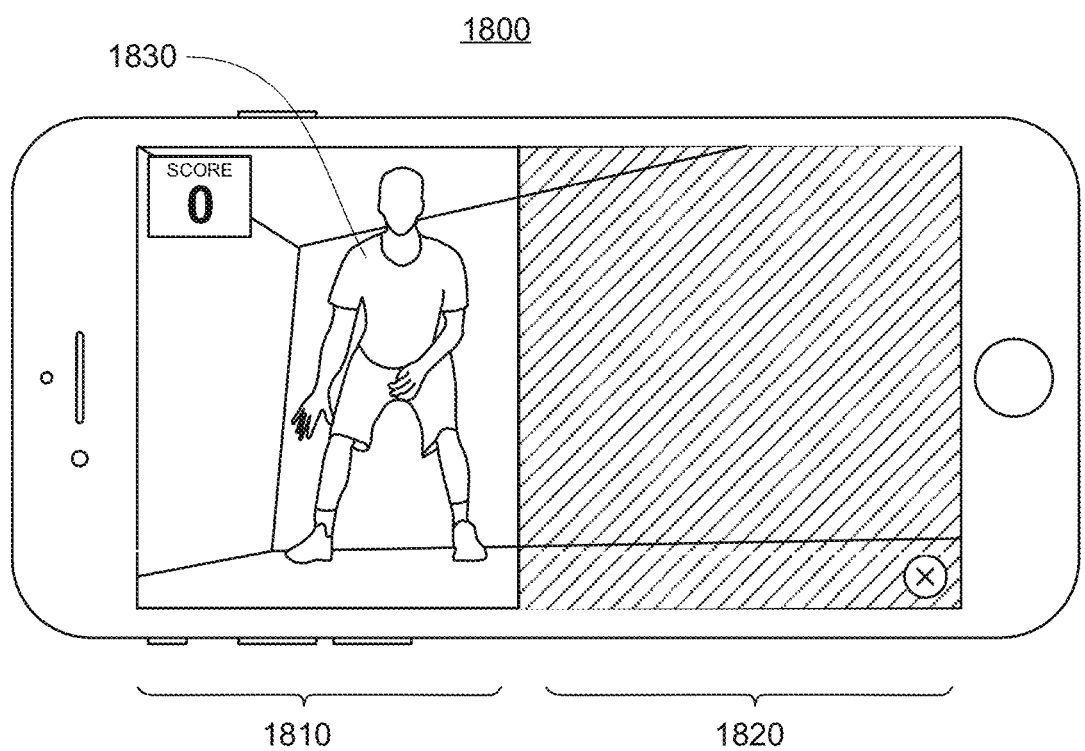
FIG. 18 is a diagram representing an exemplary interactive virtual coaching and training application running on a mobile computing device, which facilitates another exemplary interactive training activity, according to some embodiments of the present invention.

FIG. 18 is a diagram 1800 of another exemplary interactive training activity facilitated by an exemplary interactive virtual coaching and training application running on a mobile computing device, according to some embodiments of the present invention. While the examples described herein so far have been mainly directed to the user performing a dribbling movement while virtually touching virtual symbols presented to the user at the display of a user device, other training exercises may be facilitated as well. In this example, a lateral movement training exercise is presented to a user 1830, in which user 1830 waits for one or more on-screen cues such as the shading in area 1820. The user may then react to the on-screen cues by laterally moving himself out of area 1810 in which he is currently located to shaded area 1820. In alternative embodiments, area 1810 may be shaded as a cue and the user may respond by moving laterally out of area 1810 correspondingly. In some embodiments, the training area may be divided into more than one area for player 1830 to move into and/or out of. Also, an arrow or other virtual symbols may be used to designate the area for user 1830 to move into or out of. Lateral movement training without ball dribbling is suitable for home practice in a living room instead of on a ball court.

In this particular exemplary training exercise, the level of difficulty of the training session may progress and be contingent on the amount of time spent by the user in area 1810. When the user chooses to perform the training with a basketball to make it into a lateral dribbling exercise, the level of difficulty of the training session may also depend on the number and frequency of dribble mistakes, other undesirable behavior as defined by the game and/or training session, combinations thereof, and/or the like. In various embodiments, such complementary training session may be helpful in allowing the user to better train for a given sport such as the game of basketball. By introducing a way to train for lateral movement quickness as described by this example training exercise, this particular exercise may serve to mimic aspects of gameplay, such as avoiding defenders on the court.

In some embodiments, one or more human trainers such as a partner or a coach may be integrated into the training sessions described herein. For example, a human trainer may provide cones for users to dribble around to mimic defenders, and the NEX system may provide randomly generated visual cues around such cones or audio cues for users to dribble or move in a particular order or pattern. A human trainer or a ball shooting machine may also feed balls continuously to a user, and the NEX system may provide additional cues, visual or audio, as instructions for a next set of movements. Such advanced training techniques may be better suited to describing real-world gaming situations where obstacles are not static and may be unpredictable.

In various embodiments, the following additional implementation possibilities are contemplated to be within the scope of the present invention. These exemplary embodiments are for illustrative purposes only and do not limit the scope of the present invention.

(1) A virtual coaching and performance training system that facilitates training sessions to monitor cross-over style movements in the game of basketball.

(2) A virtual coaching and performance training system which facilitates training sessions that incorporate various dribble challenges, for example to dribble uninterrupted for a number of times, to dribble with one hand only while keeping the other hand fixed, to dribble with one hand in a particular pattern such as around a shape of figure "8", or to switch among different dribbling types including front dribble, behind-the-back dribble, under-the-leg dribble and the like.

(3) A virtual coaching and performance training system which facilitates multi-player training, as described with reference to FIG. 7.

(4) A virtual coaching and performance training system that allows a training video to be sent via a communications interface to a television viewing medium, such as AirPlay to an AppleTV. As discussed previously with reference to FIG. 1D, an external display such as a television or a projector may be coupled to the mobile computing device, such that the user may see the captured training video and virtual training cues and information with higher resolution and better clarity. By having a wireless connection to a larger display device, the user may also train at a larger distance away from the mobile computing device over a larger training area.

(5) A virtual coaching and performance training system that places the user in an augmented reality (AR) environment, possibly using additional equipment such as head mounted displays and/or projection lamps integrated into the system. For example, instead of editing or annotating a recorded training video file or stream, a projection lamp coupled to the mobile computing device may be used to project a visual cue onto a projection of the training video, as an augmentation of the training video. The training video may be analyzed while taking into consideration of the projected visual cue, to determine user posture flows and user responses. In another example, in addition to recording the user and the training environment as the training video, additional virtual elements may be generated, optionally based on captured user inputs, and the training video may be partially or fully virtualized to place the user in an AR or virtual reality (VR) environment.

(6) Systems, methods, and apparatuses that provide analysis and real-time and/or near real-time correction of movement patterns and postures of users during training sessions. As discussed previously, visual or audio feedback information in the form of textual messages and graphical symbols may be given to the user as the NEX system analyzes the user's posture flow.

CONCLUSIONS

One of ordinary skill in the art knows that the use cases, structures, schematics, and flow diagrams may be performed in other orders or combinations, but the inventive concept of the present invention remains without departing from the broader scope of the invention. Every embodiment may be unique, and methods/steps may be either shortened or lengthened, overlapped with the other activities, postponed, delayed, and continued after a time gap, such that every end-user device is accommodated by the server to practice the methods of the present invention.

The present invention may be implemented in hardware and/or in software. Many components of the system, for example, signal processing modules or network interfaces etc., have not been shown, so as not to obscure the present invention. However, one of ordinary skill in the art would appreciate that the system necessarily includes these components. A computing device, as illustrated in FIG. 2, is a hardware that includes at least one processor coupled to a memory. The processor may represent one or more processors (e.g., microprocessors), and the memory may represent random access memory (RAM) devices comprising a main storage of the hardware, as well as any supplemental levels of memory, e.g., cache memories, non-volatile or back-up memories (e.g., programmable or flash memories), read-only memories, etc. In addition, the memory may be considered to include memory storage physically located elsewhere in the hardware, e.g. any cache memory in the processor, as well as any storage capacity used as a virtual memory, e.g., as stored on a mass storage device.

The hardware of a computing device also typically receives a number of inputs and outputs for communicating information externally. For interface with a user, the hardware may include one or more user input devices (e.g., a keyboard, a mouse, a scanner, a microphone, a camera, etc.) and a display (e.g., a Liquid Crystal Display (LCD) panel). For additional storage, the hardware may also include one or more mass storage devices, e.g., a floppy or other removable disk drive, a hard disk drive, a Direct Access Storage Device (DASD), an optical drive (e.g., a Compact Disk (CD) drive, a Digital Versatile Disk (DVD) drive, etc.) and/or a tape drive, among others. Furthermore, the hardware may include an interface to one or more networks (e.g., a local area network (LAN), a wide area network (WAN), a wireless network, and/or the Internet among others) to permit the communication of information with other computers coupled to the networks. It should be appreciated that the hardware typically includes suitable analog and/or digital interfaces to communicate with each other.

In some embodiments of the present invention, the entire system can be implemented and offered to the end-users and operators over the Internet, in a so-called cloud implementation. No local installation of software or hardware would be needed, and the end-users and operators would be allowed access to the systems of the present invention directly over the Internet, using either a web browser or similar software on a client, which client could be a desktop, laptop, mobile device, and so on. This eliminates any need for custom software installation on the client side and increases the flexibility of delivery of the service (software-as-a-service), and increases user satisfaction and ease of use. Various business models, revenue models, and delivery mechanisms for the present invention are envisioned, and are all to be considered within the scope of the present invention.

The hardware operates under the control of an operating system, and executes various computer software applications, components, program code, libraries, objects, modules, etc. to perform the methods, processes, and techniques described above.

In general, the method executed to implement the embodiments of the invention may be implemented as part of an operating system or a specific application, component, program, object, module or sequence of instructions referred to as "computer program(s)" or "program code(s)." The computer programs typically comprise one or more instructions set at various times in various memory and storage devices in a computing device or computer, and that, when read and executed by one or more processors in the computer, cause the computer to perform operations necessary to execute elements involving the various aspects of the invention. Moreover, while the invention has been described in the context of fully functioning computers and computer systems, those skilled in the art will appreciate that the various embodiments of the invention are capable of being distributed as a program product in a variety of forms, and that the invention applies equally regardless of the particular type of machine or computer-readable media used to actually effect the distribution. Examples of computer-readable media include but are not limited to recordable type media such as volatile and non-volatile memory devices, floppy and other removable disks, hard disk drives, optical disks (e.g., Compact Disk Read-Only Memory (CD-ROMS), Digital Versatile Disks, (DVDs), etc.), and digital and analog communication media.

Although specific embodiments of the disclosure have been described, one of ordinary skill in the art will recognize that numerous other modifications and alternative embodiments are within the scope of the disclosure. For example, any of the functionality and/or processing capabilities described with respect to a particular device or component may be performed by any other device or component. Further, while various illustrative implementations and architectures have been described in accordance with embodiments of the disclosure, one of ordinary skill in the art will appreciate that numerous other modifications to the illustrative implementations and architectures described herein are also within the scope of this disclosure.

Blocks of the block diagrams and flow diagrams support combinations of means for performing the specified functions, combinations of elements or steps for performing the specified functions, and program instruction means for performing the specified functions. It will also be understood that each block of the block diagrams and flow diagrams, and combinations of blocks in the block diagrams and flow diagrams, may be implemented by special-purpose, hardware-based computer systems that perform the specified functions, elements or steps, or combinations of special-purpose hardware and computer instructions.

A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform.

A software component may be stored as a file or other data storage construct. Software components of a similar type or functionally related may be stored together such as, for example, in a particular directory, folder, or library. Software components may be static (for example, pre-established or fixed) or dynamic (for example, created or modified at the time of execution).

Software components may invoke or be invoked by other software components through any of a wide variety of mechanisms. Invoked or invoking software components may comprise other custom-developed application software, operating system functionality (for example, device drivers, data storage (for example, file management) routines, other common routines and services, etc.), or third-party software components (for example, middleware, encryption, or other security software, database management software, file transfer or other network communication software, mathematical or statistical software, image processing software, and format translation software).

Software components associated with a particular solution or system may reside and be executed on a single platform or may be distributed across multiple platforms. The multiple platforms may be associated with more than one hardware vendor, underlying chip technology, or operating system. Furthermore, software components associated with a particular solution or system may be initially written in one or more programming languages but may invoke software components written in another programming language.

Computer-executable program instructions may be loaded onto a special-purpose computer or other particular machine, a processor, or other programmable data processing apparatus to produce a particular machine, such that execution of the instructions on the computer, processor, or other programmable data processing apparatus causes one or more functions or operations specified in the flow diagrams to be performed. These computer program instructions may also be stored in a computer-readable storage medium (CRSM) that upon execution may direct a computer or other programmable data processing apparatus to function in a particular manner, such that the instructions stored in the computer-readable storage medium produce an article of manufacture including instruction means that implement one or more functions or operations specified in the flow diagrams. The computer program instructions may also be loaded onto a computer or other programmable data processing apparatus to cause a series of operational elements or steps to be performed on the computer or other programmable apparatus to produce a computer-implemented process.

Although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Although the present invention has been described with reference to specific exemplary embodiments, it will be evident that the various modification and changes can be made to these embodiments without departing from the broader scope of the invention. Accordingly, the specification and drawings are to be regarded in an illustrative sense rather than in a restrictive sense. It will also be apparent to the skilled artisan that the embodiments described above are specific examples of a single broader invention which may have greater scope than any of the singular descriptions taught. There may be many alterations made in the descriptions without departing from the scope of the present invention.

What is claimed is:

1. A non-transitory storage medium, the non-transitory storage medium storing executable instructions, the executable instructions when executed by a hardware processor causes the hardware processor to execute a process for facilitating multi-player training of body-eye coordination using mobile computing devices each having a camera, the non-transitory storage medium comprising executable instructions to:
   capture a first training video of a first player, using a first camera on a first mobile computing device;
   superimpose a visual cue onto the first training video at a visual cue location and for a cue period starting from a first time instant;
   determine whether the first player has responded to the visual cue at a second time instant within the cue period, by analyzing a body posture flow of the first player between the first time instant and the second time instant, wherein the body posture flow of the first player is extracted from the first training video by performing a computer vision algorithm on one or more frames of the first training video;
   receive a notification from a second mobile computing device, wherein the notification was generated in response to determining that a second player has responded to the visual cue at a third time instant within the cue period; and
   in response to a determination that the first player has responded to the visual cue and to the notification, generate a feedback to the first player.

2. The non-transitory storage medium of claim 1, wherein the executable instructions to determine that the second player has responded to the visual cue at the third time instant within the cue period comprises executable instructions to analyze a second body posture flow of the second player between the first time instant and the third time instant, wherein the second body posture flow of the second player was extracted from a second training video of the second player by performing the computer vision algorithm on one or more frames of the second training video, wherein the second training video was captured using a second camera on the second mobile computing device, and wherein the visual cue was superimposed onto the second training video at the visual cue location starting from the first time instant.

3. The non-transitory storage medium of claim 1, further comprising executable instructions to:
   generate the feedback based on an identity of at least one player that responded.

4. The non-transitory storage medium of claim 1, wherein the visual cue is a symbol superimposed onto the first training video at a first location of an image plane of the first training video.

5. The non-transitory storage medium of claim 4, wherein the executable instructions to determine whether one of the first player and the second player has responded to the visual cue comprises executable instructions to determine a player movement to virtually touch the symbol in the image plane with a body part.

6. The non-transitory storage medium of claim 4, wherein the executable instructions to determine whether one of the first player and the second player has responded to the visual cue comprises executable instructions to determine whether at least one player has virtually touched the symbol in the image plane with a sports equipment object.

7. The non-transitory storage medium of claim 1, wherein the executable instructions to determine whether one of the first player and the second player has responded to the visual cue comprises program code to determine whether at least one player has performed a predetermined sequence of movements.

8. The non-transitory storage medium of claim 1, further comprising executable instructions to:
determine a reaction time as a duration between the first time instant and the second time instant, wherein the feedback is a quality score generated based on the reaction time.

9. The non-transitory storage medium of claim 1, wherein the training comprises a plurality of difficulty levels based at least in part on a duration of the cue period.

10. The non-transitory storage medium of claim 1,
wherein the computer vision algorithm comprises a Convolutional Neural Network (CNN) for detecting one or more key points of the first player in an image plane, and
wherein the CNN has been trained using one or more prior videos.

11. The non-transitory storage medium of claim 1,
wherein the training video comprises a dribbling activity, and
wherein the executable instructions to superimpose the first training video with the visual cue is in response to determining that at least one player has dribbled for a predetermined number of times before the first time instant.

12. The non-transitory storage medium of claim 1, further comprising executable instructions to:
wait for a period of wait time before the executable instructions superimpose the first training video with the visual cue, wherein a duration of the wait time is based on a detected player action during the wait time.

13. The non-transitory storage medium of claim 1,
wherein the first training video comprises a juggling activity, and
wherein to superimpose the first training video with the visual cue is in response to determining that at least one player has juggled for a predetermined number of times before the first time instant.

14. The non-transitory storage medium of claim 1, further comprising executable instructions to:
generate a training statistic for at least one player based on the first training video, wherein the first training video comprises a dribbling activity performed by the first player, and wherein the training statistic includes at least one of a reaction speed and a dribbling speed.

15. The non-transitory storage medium of claim 14, wherein the training statistic comprises a first current statistic that is associated with the first training video and a second historical statistic that is associated with one or more historical training sessions associated with at least one player.

16. The non-transitory storage medium of claim 1, wherein the feedback is a score.

17. The non-transitory storage medium of claim 1, wherein the first training video comprises basketball training activities.

18. The non-transitory storage medium of claim 1, further comprising executable instructions to:
receive a second notification from a third mobile computing device, wherein the second notification was generated based on a third training video of a third player, captured using a third camera on the third mobile computing device.

19. A system comprising a hardware processor and a non-transitory storage medium, the non-transitory storage medium storing executable instructions, the executable instructions when executed by the hardware processor causes the hardware processor to execute a process for facilitating multi-player training of body-eye coordination using mobile computing devices each having a camera, the executable instructions comprising instructions to:
capture a first training video of a first player, using a first camera on a first mobile computing device;
superimpose a visual cue onto the first training video at a visual cue location and for a cue period starting from a first time instant;
determine whether the first player has responded to the visual cue at a second time instant within the cue period, by analyzing a body posture flow of the first player between the first time instant and the second time instant, wherein the body posture flow of the first player is extracted from the first training video by performing a computer vision algorithm on one or more frames of the first training video;
receive a notification from a second mobile computing device, wherein the notification was generated in response to determining that a second player has responded to the visual cue at a third time instant within the cue period; and
in response to a determination that the first player has responded to the visual cue and to the notification, generate a feedback to the first player.

20. The system of claim 19, wherein the executable instructions to determine that the second player has responded to the visual cue at the third time instant within the cue period comprises executable instructions to analyze a second body posture flow of the second player between the first time instant and the third time instant, wherein the second body posture flow of the second player was extracted from a second training video of the second player by performing the computer vision algorithm on one or more frames of the second training video, wherein the second training video was captured using a second camera on the second mobile computing device, and wherein the visual cue was superimposed onto the second training video at the visual cue location starting from the first time instant.

* * * * *